US012682454B1

(12) United States Patent
Goodwin et al.

(10) Patent No.: US 12,682,454 B1
(45) Date of Patent: Jul. 14, 2026

(54) FRAMEWORK FOR DETECTING DISCREPANCIES BETWEEN IMAGES AND IMAGE INTERPRETATIONS

(71) Applicant: Amazon Technologies, Inc., Seattle, WA (US)

(72) Inventors: Travis Reed Goodwin, Seattle, WA (US); Joseph Paul Cohen, Seattle, WA (US); Han-Chin Shing, Seattle, WA (US); Emine Busra Celikkaya, Seattle, WA (US); Isabel Ullman, Seattle, WA (US); Minal Vinay Kucheria, Seattle, WA (US)

(73) Assignee: Amazon Technologies, Inc., Seattle, WA (US)

( * ) Notice: Subject to any disclaimer, the term of this patent is extended or adjusted under 35 U.S.C. 154(b) by 354 days.

(21) Appl. No.: 18/368,889

(22) Filed: Sep. 15, 2023

(51) Int. Cl.
| | |
|---|---|
| *G06T 7/00* | (2017.01) |
| *G06F 40/30* | (2020.01) |
| *G16H 30/20* | (2018.01) |

(52) U.S. Cl.
CPC ............ *G06T 7/0012* (2013.01); *G06F 40/30* (2020.01); *G16H 30/20* (2018.01); *G06T 2207/10081* (2013.01); *G06T 2207/10088* (2013.01); *G06T 2207/10101* (2013.01); *G06T 2207/10116* (2013.01); *G06T 2207/10132* (2013.01); *G06T 2207/20081* (2013.01); *G06T 2207/30196* (2013.01)

(58) Field of Classification Search
None
See application file for complete search history.

(56) References Cited

U.S. PATENT DOCUMENTS

| | | | | |
|---|---|---|---|---|
| 2011/0029922 | A1* | 2/2011 | Hoffberg | .......... H04N 21/44008 |
| | | | | 715/811 |
| 2020/0043600 | A1* | 2/2020 | Glottmann | ............. G16H 50/20 |
| 2020/0160993 | A1* | 5/2020 | Xie | ....................... G06T 7/0012 |

FOREIGN PATENT DOCUMENTS

WO      WO-2024180126  A1 *  9/2024   .......... G06N 3/0895

* cited by examiner

*Primary Examiner* — Thomas D Lee
(74) *Attorney, Agent, or Firm* — Nicholson De Vos Webster & Elliott LLP

(57) ABSTRACT

Systems and techniques are disclosed for determining discrepancies between conditions and parameters associated with an image. An image processing model may generate output indicating predicted values for an image using the image as input, while a text processing model may generate output indicating corresponding predicted values for an image using textual data associated with the image as input. A comparison of the output data may be performed to determine discrepancies between values. Discrepancies that are sufficiently significant and relevant may be reported for additional analysis.

20 Claims, 9 Drawing Sheets

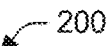

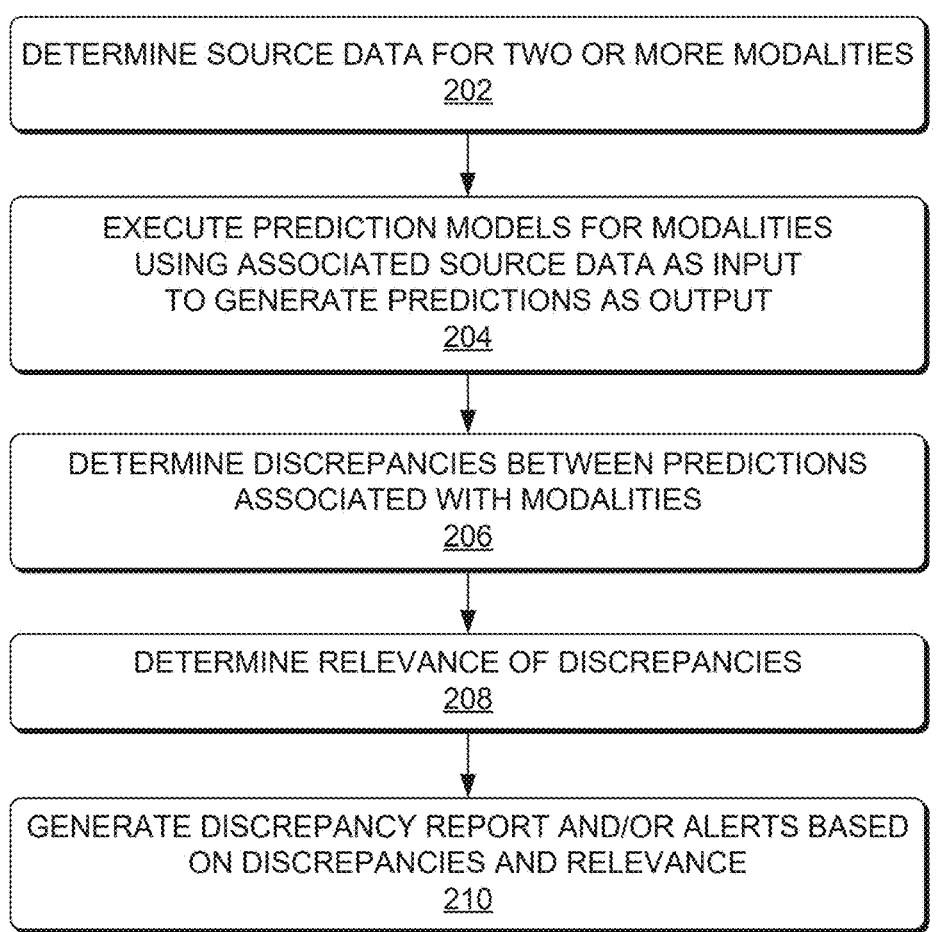

DETERMINE SOURCE DATA FOR TWO OR MORE MODALITIES
202

EXECUTE PREDICTION MODELS FOR MODALITIES
USING ASSOCIATED SOURCE DATA AS INPUT
TO GENERATE PREDICTIONS AS OUTPUT
204

DETERMINE DISCREPANCIES BETWEEN PREDICTIONS
ASSOCIATED WITH MODALITIES
206

DETERMINE RELEVANCE OF DISCREPANCIES
208

GENERATE DISCREPANCY REPORT AND/OR ALERTS BASED
ON DISCREPANCIES AND RELEVANCE
210

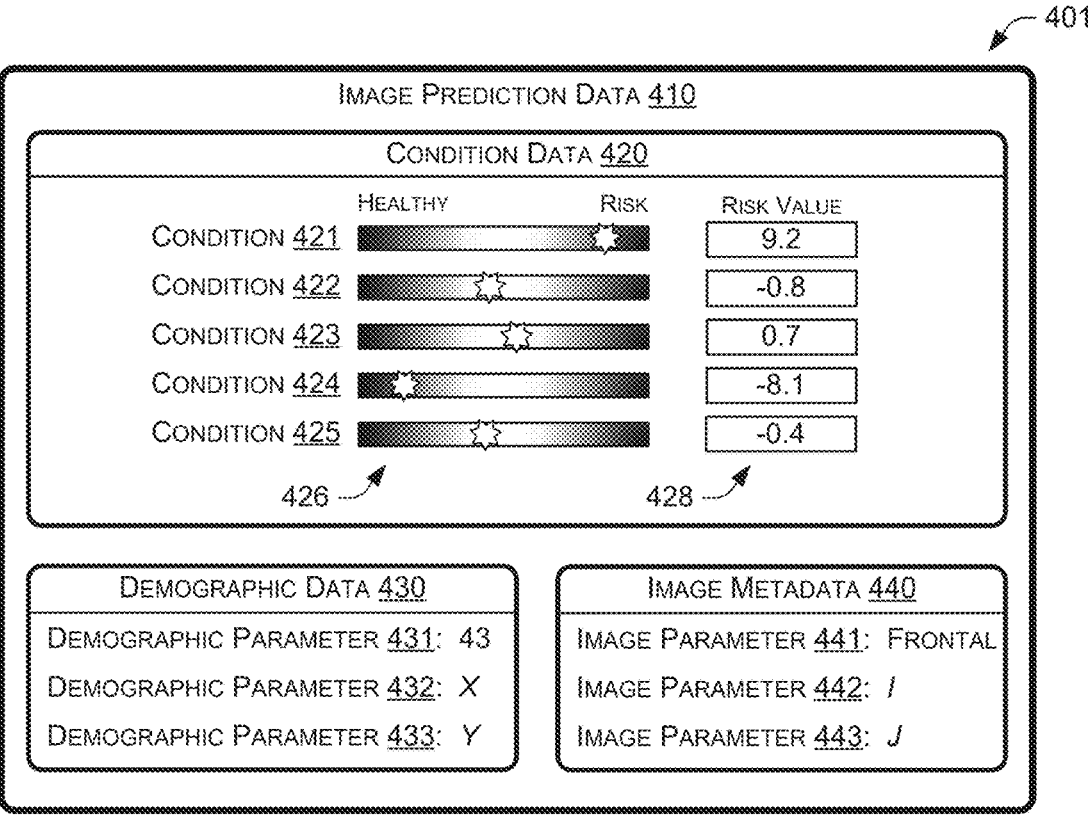

IMAGE PREDICTION DATA 410

CONDITION DATA 420

| | HEALTHY      RISK | RISK VALUE |
|---|---|---|
| CONDITION 421 | | 9.2 |
| CONDITION 422 | | -0.8 |
| CONDITION 423 | | 0.7 |
| CONDITION 424 | | -8.1 |
| CONDITION 425 | | -0.4 |

426          428

DEMOGRAPHIC DATA 430

DEMOGRAPHIC PARAMETER 431: 43

DEMOGRAPHIC PARAMETER 432: X

DEMOGRAPHIC PARAMETER 433: Y

IMAGE METADATA 440

IMAGE PARAMETER 441: FRONTAL

IMAGE PARAMETER 442: I

IMAGE PARAMETER 443: J

TEXT PREDICTION DATA 450

CONDITION DATA 460

| | HEALTHY      RISK | RISK VALUE |
|---|---|---|
| CONDITION 421 | | -3.4 |
| CONDITION 422 | | -0.2 |
| CONDITION 423 | | 0.6 |
| CONDITION 424 | | -7.9 |
| CONDITION 425 | | -0.3 |

466          468

DEMOGRAPHIC DATA 470

DEMOGRAPHIC PARAMETER 431: 13

DEMOGRAPHIC PARAMETER 432: X

DEMOGRAPHIC PARAMETER 433: Y

IMAGE METADATA 480

IMAGE PARAMETER 441: SIDE

IMAGE PARAMETER 442: Q

IMAGE PARAMETER 443: J

FIG. 4B

PREDICTION
DETERMINATION
114

DISCREPANCY
DETERMINATION
134

DISCREPANCY REPORT
GENERATION
138

CRYPTOGRAPHY
SERVICE
800D

STORAGE SERVICE
800A

AUTHENTICATION
SERVICE
800E

ON-DEMAND
COMPUTING SERVICE
800B

POLICY MANAGEMENT
SERVICE
800F

SERVERLESS
COMPUTE SERVICE
800C

DEPLOYMENT SERVICE
800G

DISCREPANCY DETERMINATION SYSTEM 102

FRAMEWORK FOR DETECTING DISCREPANCIES BETWEEN IMAGES AND IMAGE INTERPRETATIONS

BACKGROUND

Modern imaging technology has allowed medical personnel to more accurately identify and diagnose various medical conditions. Modern imaging technology may also be used in non-medical areas, for example, to improve the identification of internal faults in structural material and/or obscured wear and/or damage to mechanical components that may not be visible by external inspection. Images generated using modern imaging technologies may be analyzed by a user (e.g., radiologist, technician, etc.), who may draft a semantic summary and interpretation of such images that may include an identification of one or more conditions and/or diagnoses that may be represented in the image. However, such users may miss and/or misidentify various features and/or conditions that may be represented in an image. Such mistakes may be propagated into the semantic description of the image prepared by the analyzing user. Because subsequent users (e.g., doctors, engineers, etc.) may rely on the semantic representation of an image and may not have the skills, time, and/or access to interpret the image first-hand, mistakes in the semantic description of the image may result in a delayed and/or incorrect diagnosis of a problem that may be represented in the imaged subject (e.g., incorrect or missed diagnosis of a medical condition, incorrect or missed identification of a structural fault, etc.).

BRIEF DESCRIPTION OF THE DRAWINGS

The detailed description is set forth below with reference to the accompanying figures. In the figures, the left-most digit(s) of a reference number identifies the figure in which the reference number first appears. The use of the same reference numbers in different figures indicates similar or identical items. The systems depicted in the accompanying figures are not to scale and components within the figures may be depicted not to scale with each other.

FIG. 2 illustrates a flow diagram of an example method for determining discrepancies between data associated with an image and originating at two or more modalities and for generating discrepancy reports and/or alerts based on such discrepancies.

FIG. 4A illustrates a block diagram representing exemplary image prediction data that may be received, processed, and/or generated by a system implementing a discrepancy detection framework.

FIG. 4B illustrates a block diagram representing exemplary text prediction data that may be received, processed, and/or generated by a system implementing a discrepancy detection framework.

DETAILED DESCRIPTION

Figure 1:
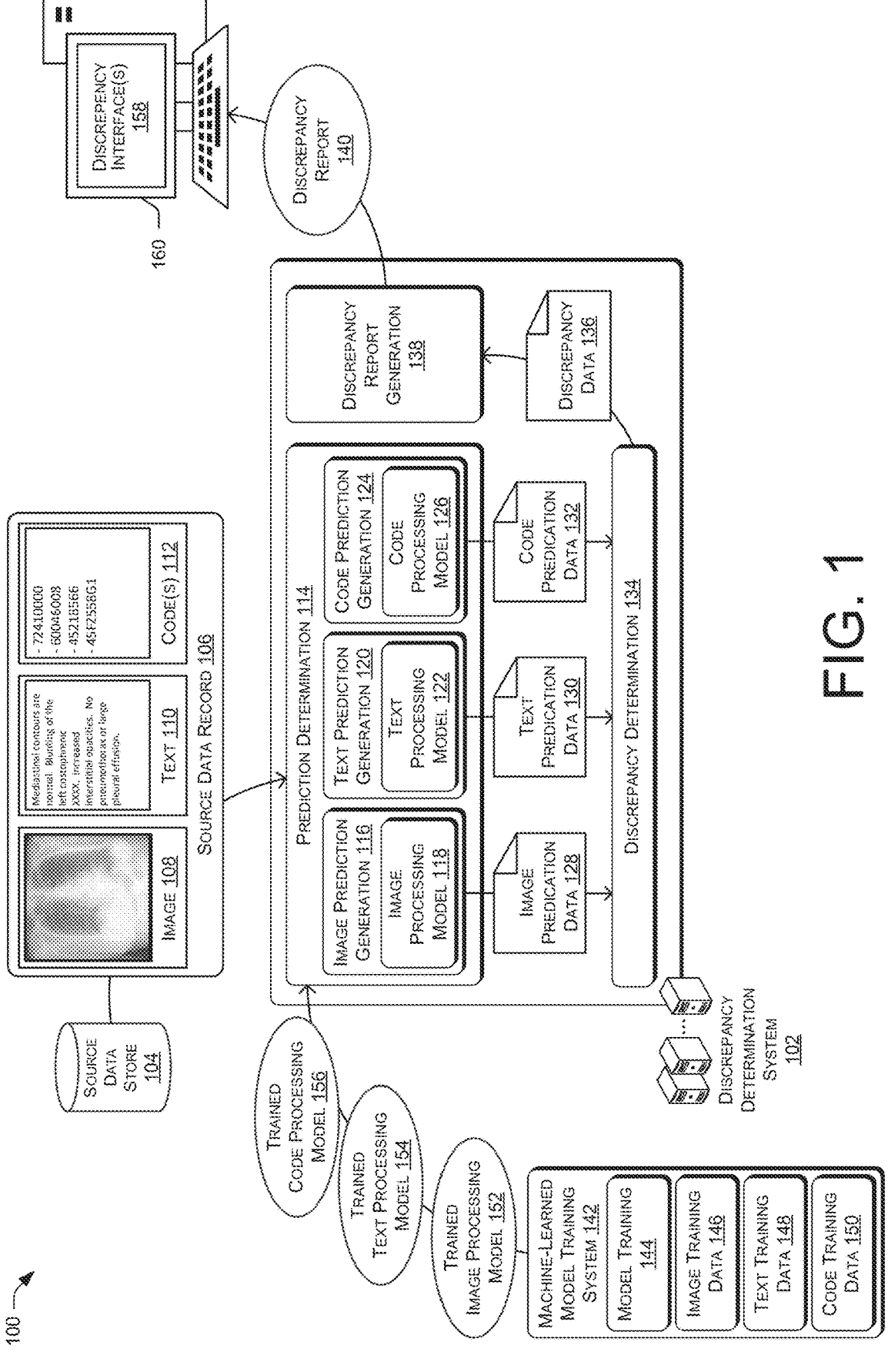
FIG. 1 illustrates a system-architecture diagram of an example environment in which a discrepancy detection framework may be implemented.

A discrepancy detection framework may be used in, or in conjunction with, a system for detecting conditions that may be represented in images. In examples, images and semantic data and/or other types of data associated with such images may be processed by a discrepancy determination system to identify discrepancies between such images and their associated data. For example, an individual image may be processed by the system using a machine-learned image processing model to determine one or more conditions that may be represented in the image. Data associated with the individual image, such as semantic data prepared by a user based on a visual analysis of the image, may be processed by the system using a machine-learned text processing model to determine one or more conditions that may be represented in the semantic data. The conditions determined based on the image processing may be compared to the conditions determined using semantic processing. Discrepancies detected between such conditions (e.g., sufficiently significant and/or relevant discrepancies) may be used to generate an alert or discrepancy report indicating the processed image and associated data. This alert and/or report may then be provided to a user for additional analysis, for example, to more definitively determine the conditions represented in the image.

In conventional systems, a human user may analyze an image to identify conditions and/or perform a diagnosis of the subject of the image. For example, a radiologist may analyze an image captured using medical imaging technology (e.g., X-ray, magnetic resonance imaging (MRI) image, computed tomography (CT) scan image, computed axial tomography (CAT) scan image, ultrasound image, histology image, optical coherence tomography (OCT) image, fundus image, histology image, pathology image, histopathology image, etc.) and generate a written or other semantic description of one or more conditions that the radiologist has identified in the image. This description of the condition(s) represented in the image may be provided to other doctors and/or users, with or without the actual image), for use in further diagnosis and treatment of the patient. As with any human-involved process, mistakes may be made. For example, the radiologist may misidentify one or more conditions and/or fail to identify one or more conditions represented in the image. The radiologist may also, or instead, introduce one or more typographical errors into the semantic description of the image and/or mistakenly select one or more incorrect options when using a semi-automated system to generate such a description for the image. This may result in incorrect diagnosis and treatment of the subject patient downstream by other doctors and/or users who may rely on the description of the image prepared by the radiologist. As will be appreciated, similar processes may be used in analyzing images of other types and similar issues may arise when mistakes are made.

A system implementing a discrepancy determination framework may receive (e.g., data indicating and/or representing) one or more images captured using any suitable imaging technology. In examples used herein, medical images and imaging technology may be used for description purposes, but the various systems and methods described herein may be used to process images of any type that may have data of any modality associated therewith. The one or more images may be associated with data that may represent identified conditions, attributes, and/or properties for the image. Such data may be manually generated, for example, by a human user analyzing an associated image. Alternatively or additionally, accompanying data may be generated by one or more automated systems. In various examples, the accompanying data may be textual data indicating conditions determined to be represented in an accompanying image. For example, a user may enter text into an interface that may store such text as data associated with an image. Alternatively or additionally, a user may select one or more values for one or more parameters from a discrete set of values for each such parameter (e.g., using checkboxes, drop-down lists, etc.) that may then be associated with an image. For example, a user may select, on an interface, one or more conditions as conditions identified by the user as being represented in the image.

Data associated with various other modalities may be associated with an image that may be processed by a system implementing a discrepancy determination framework. For example, one or more codes (e.g., medical diagnostic codes, condition codes, etc.) may be assigned to or otherwise associated with an image (e.g., by a user and/or automatically). Data associated with other processes, such as lab data and/or diagnostic data may also be associated with an image and processed as described herein to determine conditions and/or parameters for comparison to image modality conditions and/or parameters for discrepancy determination. Image metadata may also be processed using the systems and techniques described herein for discrepancy determination operations (e.g., image and imaging system data, such as date and time of image capture, image resolution, lens data, system data, type of image, etc.; manually and/or automatically generated descriptive metadata; manually and/or automatically generated administrative metadata; digital imaging and communications in medicine (DICOM) data (e.g., DICOM headers, header data, tags, etc.), etc.). Any other data of any other modality that may be associated with an image may be processed as described herein.

The system implementing a discrepancy determination framework may include an image prediction generation component that may execute one or more image processing machine-learned (ML) models using an image as input to generate indications of one or more predicted conditions as output. For example, an image prediction generation component may be configured with a neural network or other ML model that may be trained to identify various conditions that may be represented in an image. In various examples, such a network or model may be trained to identify one or more conditions from a discrete set of conditions. Such conditions may include physical and/or medical conditions, such as diseases and/or abnormalities that may be associated with increased health risks for the subject of an image (e.g., patient). Such a network or model may also, or instead, be trained to identify various parameters associated with the image and/or the demographics of the subject of the image. For example, the network or model may be trained to identify the position of the subject and/or of the imaging system when the image was captured (e.g., frontal image, side image, etc.). The network or model may also, or instead, be trained to identify the demographic data of the subject based on the image, such as age, race, sex, gender, one or more behavioral attributes, one or more environmental attributes, one or more social determinants, etc. The image prediction generation component may process an image and generate output indicating the various predicted conditions and parameters identified by the image processing ML model(s).

The system implementing a discrepancy determination framework may further include a text prediction generation component that may execute one or more text processing machine-learned (ML) models using textual data associated with an image as input to generate indications of one or more predicted conditions as output. For example, a text prediction generation component may be configured with a neural network or other ML model that may be trained to identify various conditions that may be described in textual data associated with an image. Here again, such a network or model may be trained to identify one or more conditions from a discrete set of conditions, such as the discrete set of conditions on which the image processing ML model may have been trained. As with the image processing model, such conditions may include physical and/or medical conditions, such as diseases and/or abnormalities that may be associated with increased health risks for the subject of an image (e.g., patient). Such a network or model may also, or instead, be trained to identify various demographic and/or image parameters that may be represented in the textual data associated with the image. For example, the network or model may be trained to identify the position of the subject and/or of the imaging system indicated in textual data associated with an image. The network or model may also, or instead, be trained to identify the demographic data of the subject indicated in textual data associated with an image. The text prediction generation component may process textual data associated with an image to generate output indicating the various predicted conditions and parameters identified by the text processing ML model(s).

Other models and/or prediction generation components may be configured within a discrepancy determination framework. For example, codes of various types may be associated with an image that may represent various conditions and/or parameters. For instance, medical codes indicating particular conditions may be assigned to an image by a user. Data representing such codes may be processed by a code prediction generation component, in examples using one or more code processing ML models, to determine predicted conditions and/or parameters for the image. In examples, image metadata may be processed to determine predicted conditions and/or parameters for the image. An image metadata prediction generation component may determine, for example, from DICOM data, one or more image parameters that may then be used in discrepancy determination operations as described herein. Such image metadata prediction generation component may include one or more machine-learned models and/or may interpret DICOM data and/or other image metadata using various operations to determine image parameters. Other types of data, received in any form, may be processed within a discrepancy determination framework as described herein to determine conditions and/or parameters that may be used to determine discrepancies between modalities.

In various examples, the output of the prediction generation components described herein may represent predicted conditions and/or parameters as probabilities and/or discrete values. For example, one or more of the models described herein executed by such prediction generation components may be trained to generate, as output, a probability for each of a discrete number of conditions or parameters (e.g., a probability that the condition is represented in the associated image). In examples, one or more of the models described herein executed by such prediction generation components may be trained to generate, as output, a discrete predicted value for one or more conditions or parameters (e.g., a particular value for demographic data, such as "13" or 23" for age; a particular value for subject position data, such as "side" or "frontal;" etc.). In examples, one or more of the models described herein executed by such prediction generation components may be trained to generate, as output, a range of predicted values for one or more conditions or parameters (e.g., a range of values for demographic data, such as "between 20 and 30" for age; a particular range of values for condition data, such as "low to medium likelihood" of a condition being present; etc.). In examples, one or more of the models described herein executed by such prediction generation components may be trained to generate, as output, a risk level for one or more conditions or parameters (e.g., a risk level value for a particular medical condition). In examples, one or more of the models described herein executed by such prediction generation components may be trained to generate, as output, a confidence of the existence or presence of one or more conditions or parameters (e.g., a confidence that a particular medical condition exists in a patient based on the input data). In examples, one or more of the models described herein executed by such prediction generation components may be trained to generate, as output, a binary value for one or more conditions or parameters (e.g., "risk" or "no risk," "present" or "not present," "detected" or "not detected," etc. for a particular medical condition). For any output of the one or more of the models described herein executed by such prediction generation components, the prediction generation components may also provide, as output, a confidence of the output value for the one or more conditions or parameters. For example, a prediction generation component may output a particular value for a medical condition and a confidence associated with that particular value (e.g., a confidence in the accuracy of the value).

The resulting predicted conditions and parameters associated with particular modalities may be compared to one another within the discrepancy determination framework to identify discrepancies between such predictions. For example, the individual models and/or prediction generation components associated with the various modalities may be configured to determine predicted values for a predetermined set of conditions and parameters. For a particular image, a value predicted by an image prediction generation component for an individual condition or parameter may be compared to a corresponding value for that individual condition predicted by a text prediction generation component (and/or code prediction generation component, image metadata prediction generation component, etc.). If a discrepancy between these values for that individual condition is identified, a significance of the discrepancy may be determined. If the discrepancy is sufficiently significant, the system may store or otherwise indicate that this individual condition is associated with a discrepancy for further processing as described herein. Each of the conditions and/or parameters in a predetermined set of conditions and parameters may be processed in this manner by a discrepancy determination component to determine a set of discrepancy data for a particular image to be further processed within the discrepancy determination framework as described herein.

The significance of a discrepancy may be determined by the discrepancy determination component based on various factors. Such factors may be user-configured and/or dynamically determined. For example, a particular condition or parameter may be associated with a discrepancy threshold that may be met for a discrepancy of that particular condition or parameter to be considered significant. For instance, a predicted medical condition may be represented (e.g., in output from a model) as a probability. The predicted medical condition may have an associated discrepancy threshold represented as a difference between two such values.

For example, if there is a discrepancy between a first probability of the predicted medical condition for a first modality (e.g., as determined by a first prediction generation component associated with the first modality) and a second probability of the predicted medical condition for a second modality (e.g., as determined by a second prediction generation component associated with the second modality) that is greater than the discrepancy threshold, the discrepancy may be indicated as significant. Otherwise, the discrepancy may be indicated as insignificant or otherwise not indicated (e.g., ignored). For instance, if the first probability may be represented as 0.75, the second probability may be represented as 0.78, and the discrepancy threshold may be represented as 0.25, then the discrepancy of 0.03 between the first probability and the second probability would not meet the discrepancy threshold, and thus the discrepancy may not be considered significant. On the other hand, if the first probability may be represented as 0.75, the second probability may be represented as 0.28, with the discrepancy threshold still represented as 0.25, then the discrepancy of 0.48 between the first probability and the second probability would meet the discrepancy threshold, and therefore the discrepancy may be considered significant.

In another example, if there is a discrepancy between a first parameter representing a predicted age of a subject of an image for a first modality (e.g., as determined by a first prediction generation component associated with the first modality) and a second parameter representing the predicted age of a subject of an image for a second modality (e.g., as determined by a second prediction generation component associated with the second modality) that is greater than an age discrepancy threshold, the discrepancy may be indicated as significant. Otherwise, the discrepancy may be indicated as insignificant or otherwise not indicated (e.g., ignored). For instance, if the first parameter may be represented as age 45, the second parameter may be represented as age 47, and the discrepancy threshold may be represented as 10 years, then the discrepancy of two years between the first parameter and the second parameter would not meet the discrepancy threshold, and thus the discrepancy may not be considered significant. On the other hand, if the first parameter may be represented as age 45, the second parameter may be represented as age 12, with the discrepancy threshold still represented as 10 years, then the discrepancy of 33 years between the first parameter and the second parameter would meet the discrepancy threshold, and therefore the discrepancy may be considered significant. Various other techniques for determining discrepancy significance may be used, including those described elsewhere herein.

In examples, one or more discrepancy criteria other than, or in addition to, a discrepancy threshold may be used to determine whether a significant discrepancy exists between two or more values for a particular condition or parameter. For example, a difference (e.g., any difference) between discrete and/or binary values for a particular parameter or condition may be a discrepancy criterion (e.g., "present" and "not present" as two values for a particular condition may be a discrepancy). In examples, a discrepancy confidence may be determined and then used to determine if a significant discrepancy is present. For instance, a discrepancy determination component may determine, based on any of a variety of criteria, a confidence of a discrepancy between two or more values for a particular condition or parameter. The discrepancy determination component may then determine whether that confidence is sufficiently high to indicate that a discrepancy exists (e.g., if the determined discrepancy confidence meets a discrepancy confidence threshold). Any other criteria may be used, in any combination, to determine the existence and/or probability of a discrepancy between two or more values for a particular condition or parameter.

In various examples, the discrepancy determination component may generate discrepancy data for a particular image that may include indications of determined significant discrepancies. This discrepancy data may further include other data, including image data, source data, and/or predicted conditions and/or parameter data. In examples, discrepancy data may be augmented image data, source data, and/or predicted conditions and/or parameter data, augmented with the determined discrepancy data.

The discrepancy determination component may provide the discrepancy data to a discrepancy report generation component for generation of discrepancy alerts and/or reports. In examples, some discrepancies may not be reportable regardless of significance. For example, the discrepancy report generation component may determine which, if any, of the significant discrepancies represented in the discrepancy data are relevant. For those that are relevant, the discrepancy report generation component may generate an alert that may indicate to a user (e.g., via a user interface) that the significant discrepancy exists. For those that are not relevant, the discrepancy report generation component may not generate an alert or may otherwise not indicate to the user that the discrepancy exists.

In examples, the relevance of particular conditions and/or parameters may be configured by a user. For example, a user may be operating a system in communication with the discrepancy determination to analyze the accuracy of a particular user's detection of a particular condition. The operating user may configure the discrepancy report generation component with a relevance filter that may be used to disregard or otherwise not alert conditions and/or parameters that are unrelated to the particular condition and/or otherwise not of interest to the operating user.

The discrepancy report generation component may transmit generated discrepancy reports and/or alerts to one or more users for further evaluation. For those images that are not associated with significant discrepancies (e.g., the data across modalities is substantially congruent), the system may store an indication of such determinations and/or may also transmit a report reflecting the substantially congruent condition and parameter data across modalities to a user.

The disclosed systems and techniques provide a more efficient and effective means of determining discrepancies between modalities that may be associated with an image. By facilitating a more efficient determination of such discrepancies, the examples described herein may provide faster and more efficient means of identifying potential misdiagnoses and/or missed diagnoses, which may in turn reduce health risk and medical costs. For example, in the disclosed system, discrepancies between conditions represented on an image and those described by a user as being represented in the image are identified using the disclosed systems and techniques, while those images without such discrepancies are removed from further processing, thereby greatly reducing the quantity of images that must be reevaluated by a human user and/or further processed by a discrepancy analysis system. By removing from the processing pipeline those images without significant discrepancies sooner, the number of processor cycles needed to process (e.g., substantially congruent) images, memory resources to store images and image data, and network resources required to exchange images and image data may be reduced. Furthermore, by providing images for further analysis that are more likely to be associated with errors, resources (human and otherwise) are not wasted processing images that are less likely to be associated with errors. Thus, the disclosed systems and techniques improve the user experience while minimizing inefficacies, increasing available network bandwidth (and thereby reducing latency), increasing available memory for other processes and operations, and improving overall system performance.

The techniques and systems described herein may be implemented in a number of ways. Example implementations and additional details are provided below with reference to the following figures.

FIG. 1 is a block diagram of an illustrative environment 100 that may be a portion of, or otherwise associated with, a system incorporating a discrepancy determination framework or any other type of data processing and/or storage system. The environment 100 may include a discrepancy determination system 102 and a machine-learned model training system 142. The environment 100 may also include a source data store 104 that may be one or more data storage systems of any type. The systems 102 and 142, as well as the data store 104, may each represent one or more physical and/or logical resources, such as one or more server computers, virtual machines, software resources, databases, notebooks clusters, datasets, etc., or any combination thereof.

The discrepancy determination system 102 may be configured to receive source data from the source data store 104. Source data may be one or more images and associated data of one or more other modalities. For example, the discrepancy determination system 102 may receive a source data record 106 that may include or otherwise indicate an image 108, text 110, and one or more codes 112. The image 108 may be an image of any type captured by an imaging system (e.g., X-ray, scan, etc.) and/or data representative thereof. In a non-limiting example that will be used throughout the description of FIG. 1, the image 108 may be a digital representation of an X-ray. The text 110 may be textual data associated with the image 108. For example, the text 110 may be text entered and/or selected by a user for association with the image 108. For instance, where the image 108 is an X-ray, the text 110 may be a description of conditions and/or parameters identified in the X-ray by a radiologist. The code(s) 112 may be code data associated with the image 108. For example, the code(s) 112 may be codes selected by a user as representing one or more conditions and/or parameters for association with the image 108. For instance, where the image 108 is an X-ray, the code(s) 112 may be a description of conditions and/or parameters identified in the X-ray by a radiologist.

The source data record 106 may be transmitted to, acquired by, accessed, or otherwise received at a prediction determination component 114 of the discrepancy determination system 102. The prediction determination component 114 may include one or more components configured to determine prediction data for individual modalities that may be associated with an image. Prediction data may be any value or range of values determined for a particular condition or parameter. For example, for a particular condition (e.g., medical condition), a prediction value may be a likelihood of that condition being represented in the associated image. In another example, for a particular condition (e.g., medical condition), a prediction value may be an indication that the condition is present in the associated image based on a likelihood. For instance, a prediction generation component may determine that the likelihood of the condition being present in the subject of the image is over a threshold likelihood of 80%, and therefore may set the prediction value for the particular condition to an indication that the condition is present (e.g., "yes," "present," "likely," "high risk," etc.). In another example, for a particular parameter (e.g., age of the subject of the image), a prediction value may be an estimated age of the subject.

In examples, the prediction determination component 114 may include an image prediction generation component 116. The image prediction component 116 may be configured to process image modality data, such as the image 108. The image prediction generation component 116 may include an image processing model 118 that may be a machine-learned model trained to identify conditions and/or parameters in an image. In examples, the image processing model 118 may be configured to determine prediction values for conditions and parameters of a set of conditions and parameters. The image prediction component 116 may provide an image (e.g., image 108) as input to the image processing model 118 and execute the image processing model 118 to generate output that includes predicted values for conditions and parameters of the set of conditions and parameters. The image prediction component 116 may use this output to generate image prediction data 128. In examples, the image prediction data 128 may include the (e.g., unmodified) output of the image processing model 118. Alternatively or additionally, the image prediction data 128 may include data resulting from processing of the output of the image processing model 118 by the image prediction component 116 (e.g., predicted values determined by the image prediction component 116 based on the output of the image processing model 118).

In examples, the prediction determination component 114 may also, or instead, include a text prediction generation component 120. The text prediction generation component 120 may be configured to process text modality data, such as the text 110. The text prediction generation component 120 may include a text processing model 122 that may be a machine-learned model trained to identify conditions and/or parameters in textual data. In examples, the text processing model 122 may be configured to determine prediction values for conditions and parameters of a set of conditions and parameters (e.g., the same set of conditions and parameters for which the image processing model 118 is configured). The text prediction generation component 120 may provide textual data (e.g., text 110) as input to the text processing model 122 and execute the text processing model 122 to generate output that includes predicted values for conditions and parameters of the set of conditions and parameters. The text prediction generation component 120 may use this output to generate text prediction data 130. In examples, the text prediction data 130 may include the (e.g., unmodified)

output of the text processing model 122. Alternatively or additionally, the text prediction data 130 may include data resulting from processing of the output of the text processing model 122 by the text prediction generation component 120 (e.g., predicted values determined by text prediction generation component 120 based on the output of the text processing model 122).

The prediction determination component 114 may also, or instead, include a code prediction generation component 124. The code prediction generation component 124 may be configured to process code modality data, such as the code(s) 112. The code prediction generation component 124 may include a code processing model 126 that may be a machine-learned model trained to identify conditions and/or parameters in code data. In examples, the code processing model 126 may be configured to determine prediction values for conditions and parameters of a set of conditions and parameters (e.g., the same set of conditions and parameters for which the image processing model 118 and/or the text processing model 122 is configured). The code prediction generation component 124 may provide code data (e.g., code(s) 112) as input to the code processing model 126 and execute the code processing model 126 to generate output that includes predicted values for conditions and parameters of the set of conditions and parameters. The code prediction generation component 124 may use this output to generate code prediction data 132. In examples, the code prediction data 132 may include the (e.g., unmodified) output of the code processing model 126. Alternatively or additionally, the code prediction data 132 may include data resulting from processing of the output of the code processing model 126 by the code prediction generation component 124 (e.g., predicted values determined by code prediction generation component 124 based on the output of the code processing model 126).

The output for the various modalities of the various prediction generation components of the prediction determination component 114 may be provided to a discrepancy determination component 134. The discrepancy determination component 134 may be configured to determine discrepancies for values of individual conditions and/or parameters determined for individual modalities. The discrepancy determination component 134 may be further configured to determine, for identified discrepancies, whether such discrepancies are significant. For example, as described in more detail herein, the discrepancy determination component 134 may determine whether detected discrepancies meet or exceed a discrepancy threshold for the associated condition or parameter. The discrepancy determination component 134 may generate discrepancy data 136 that may represent those discrepancies determined to be significant. The discrepancy data 136 may further include any or all of the data associated with the source data record 106, the image prediction data 128, the text prediction data 130, and/or the code prediction data 132.

The discrepancy data 136 may be provided to a discrepancy report generation component 138 that may be configured to generate a discrepancy report 140. The discrepancy report 140 may present, or facilitate presentation of, the discrepancy data 136 to a user and/or any related data. In examples, the discrepancy report generation component 138 may generate, or cause the generation of, a graphical user interface presenting the discrepancy report 140 to a user. For example, the discrepancy report generation component 138 may instruct a computing device 160 to generate one or more discrepancy interfaces 158 that may present the discrepancy report 140 and/or any associated data to a user.

As described above, the prediction determination component 114 may include prediction generation components (e.g., components 116, 120, 124) that are configured to execute one or more ML models (e.g., models 118, 122, 126) to perform one or more of the prediction value determinations functions for various conditions and/or parameters that may be associated with an image. In examples, an ML model training system 142 may be configured with a model training component 144 that trains models to generate, as output, predicted values for various conditions and/or parameters using data of particular modalities as input. For example, the model training component 144 may train an image processing model to generate, as output, predicted values for various conditions and/or parameters using image data as input to generate a trained image processing model 152. The ML model training system 142 may provide the trained image processing model 152 to the image prediction generation component 116 for use as the image processing model 118. Similarly, the model training component 144 may train a text processing model to generate, as output, predicted values for various conditions and/or parameters using textual data as input to generate a trained text processing model 154. The ML model training system 142 may provide the trained text processing model 154 to the text prediction generation component 120 for use as the text processing model 122. Likewise, the model training component 144 may train a code processing model to generate, as output, predicted values for various conditions and/or parameters using code data as input to generate a trained code processing model 156. The ML model training system 142 may provide the trained code processing model 152 to the text prediction generation component 120 for use as the code processing model 126.

The training data used by the model training component 144 may include modality-specific training data. For example, to train the trained image processing model 152, the model training component 144 may use image training data 146 that may include images and associated, identified conditions and/or parameters. To train the trained text processing model 154, the model training component 144 may use image training data 148 that may include textual data and associated, identified conditions and/or parameters. To train the trained code processing model 156, the model training component 144 may use code training data 150 that may include code data and associated, identified conditions and/or parameters.

The model training component 144 may train a model with one or more layers. For example, any or all of the trained image processing model 152, the trained text processing model 154, and the trained code processing model 156, may include one or more neural network layers trained to process input data (e.g., images, text, codes, etc.) and/or one or more language model (LM) layers trained to process, as input, output from one or more neural network layers. Any combination and number of neural networks and machine-learned models may be used to implement the prediction generation processes described herein.

The systems and methods described herein may be faster, more efficient, and more robust than conventional systems and methods for determining discrepancies in medical image analysis and other image analysis, as they may facilitate the efficient determination of images that require additional manual analysis while removing from further manual consideration those images with which no discrepancies have been identified. That is, the systems and methods described herein provide a technological improvement over existing discrepancy determination processes that involve manually evaluating individual images and associated textual and other data that may result in less thorough analysis for discrepancies and therefore more frequent missing of such discrepancies, increasing the speed and efficiency of such operations and overall outcomes, especially in a medical context. Moreover, the systems and methods described herein provide a significant increase in the relevance of recommended additional image analysis by using trained and executed machine-learned models that increase the accuracy of discrepancy determinations, while greatly reducing the likelihood of presenting images with no discrepancies to a user for additional manual analysis.

By efficiently identifying discrepancies between images and data of other modalities associated with such images, processing requirements for determining discrepancies are reduced because the frequency of performing discrepancy determination-related operations is reduced. For example, because more discrepancies are accurately identified sooner, various users may not be required to repeatedly access images and related data to analyze such images and related data for different types of discrepancies. The discrepancy determination techniques described herein further increase the efficiency of the disclosed systems and methods because more relevant discrepancy data is presented while less relevant or irrelevant discrepancy data is eliminated before presentation on an interface, thereby reducing the processing and memory requirements of the present systems and methods even further over conventional techniques. Accordingly, fewer storage resources and fewer processing resources may be required to determine and further analyze discrepancies using these systems and methods and fewer network resources are needed to transmit and receive associated data.

Figure 3:
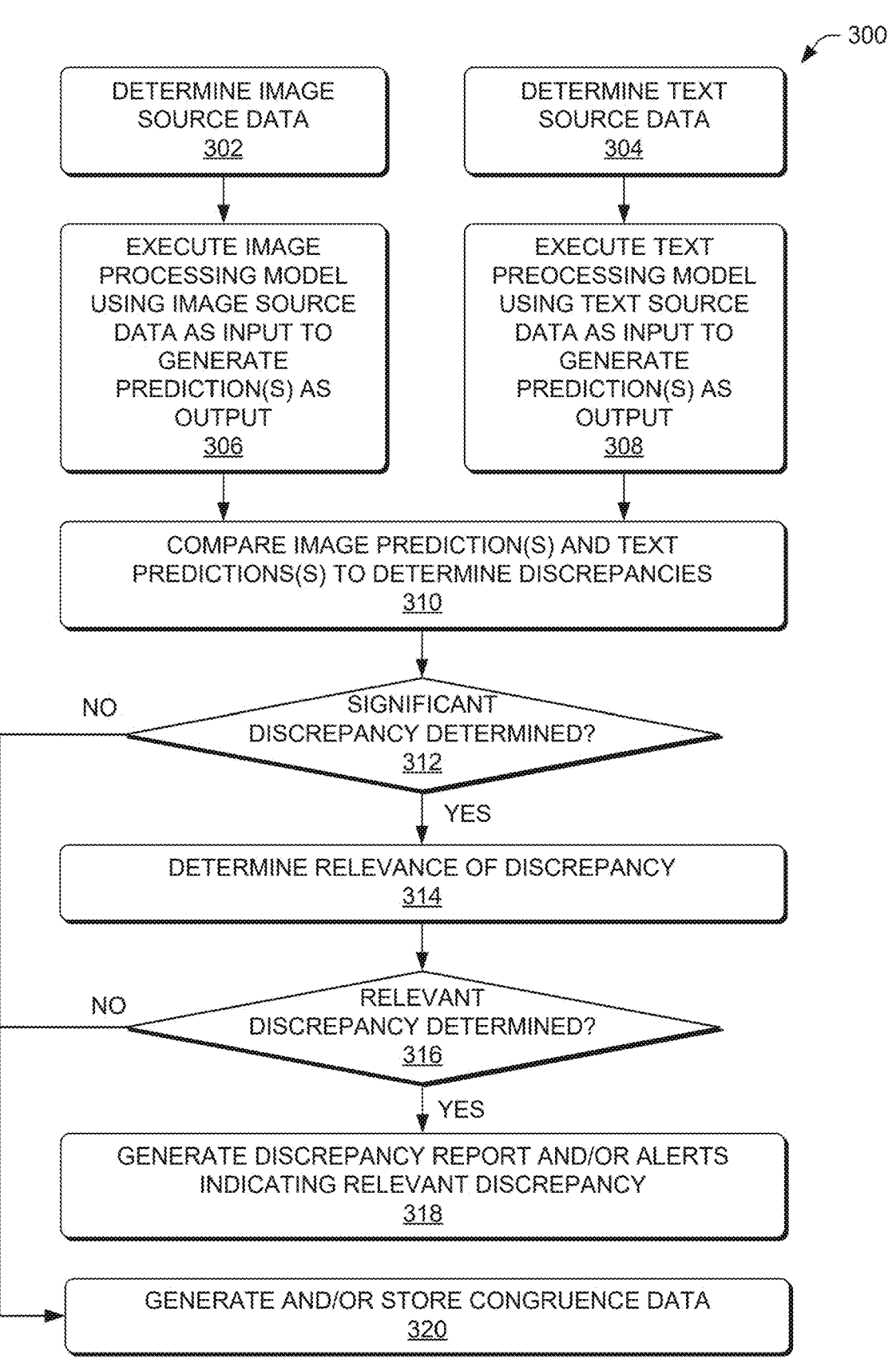
FIG. 3 illustrates a flow diagram of an example method for determining discrepancies between image data and text data associated with an image using machine-learned models and for generating discrepancy reports and/or alerts based on such discrepancies.

FIGS. 2 and 3 are flow diagrams of illustrative processes illustrated as a collection of blocks in a logical flow graph, which represent a sequence of operations that can be implemented in hardware, software, or a combination thereof. In the context of software, the blocks represent computer-executable instructions stored on one or more computer-readable storage media that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the processes.

FIG. 2 is a flow diagram of an illustrative process 200 to determine discrepancies between conditions and/or parameters associated with an image determined using two or more modalities. The process 200 may be described at times with reference to the environment 100 and may be performed by the discrepancy determination system 102, but the process 200 may also, or instead, be performed in other similar and/or different environments by other similar and/or different systems.

At 202, source data from, or associated with, two or more modalities may be determined. This operation may include receiving or otherwise acquiring such source data from a data store, a source data generation system or component, an electronic communication, etc. The source data may be associated with an image and may include data associated with two or more modalities. For example, the source data may include two or more of an image, image data, image metadata, textual data, code data, diagnostic data, lab data, and any other type of data that may be processed as described herein to determine predicted conditions and/or parameters that may be associated with an image.

At 204, the source data may be used as input to one or more machine-learned models that may be executed to generate predicted conditions and/or parameters as output. For example, the system may include machine-learned models trained to process data associated with particular modalities to generate a set of conditions and/or parameters. A first such machine-learned model may be trained to process an image as input to generate predicted values for the set of conditions and/or parameters, while a second such machine-learned model may be trained to process textual data as input to generate predicted values for the set of conditions and/or parameters. Alternatively or additionally, models may be used that have been trained to process code data, diagnostic data, lab data, etc. as input to generate predicted values for the set of conditions and/or parameters.

At 206, the resulting predicted condition and/or parameter values may be compared to determine whether any discrepancies between such values are present. For example, the system may compare a first value determined for a particular condition by a first modality component (e.g., executing an image processing machine-learned model using an image as input to generate the first value as output) to a second value determined for the same particular condition by a second modality component (e.g., executing a text processing machine-learned model using textual data associated with the image as input to generate the second value as output, executing a code prediction generation component using code data associated with the image as input to generate the second value as output, executing an image metadata prediction generation component using image metadata for the image (e.g., DICOM data) as input to generate the second value as output, etc.). If such a comparison determines a difference (e.g., of quantity or quality) between the first value and the second value, the system may determine that a discrepancy for that condition is present in the prediction data for the two modalities associated with the image. In examples, as described in more detail herein, the system may be configured to determine whether such discrepancies are significant based on various criteria.

At 208, the system may determine whether any such determined discrepancies are relevant. In examples, a relevance may be based on one or more factors that may be used to determine whether the determined discrepancy should be indicated (e.g., to a user) as a discrepancy. For example, a user may set one or more parameters at a discrepancy determination system that may indicate conditions and/or parameters of interest. The system may determine whether a condition or parameter associated with a determined discrepancy is indicated as one of these conditions and/or parameters of interest and, if so, include the determined discrepancy in a discrepancy alert and/or report (e.g., that may be transmitted or otherwise provided to the user). Other factors may also, or instead, be used to determine the relevance of a determined discrepancy between predicted values.

At 210, the system may generate a discrepancy report and/or alert indicating determined discrepancies (e.g., to a user and/or for storage at a data store). For example, the system may transmit an individual alert (e.g., as an email, present as an interface element, etc.) for each individual discrepancy determined. Alternatively or additionally, the system may transmit a discrepancy report (e.g., as an email, present as an interface element, etc.) that includes or indicates one or more determined discrepancies, for example, associated with a batch of images and associated data processed by a discrepancy determination system.

FIG. 3 is a flow diagram of an illustrative process 300 to determine discrepancies between predicted values determined using image and textual modalities. The process 300 may be described at times with reference to the environment 100 and may be performed by the discrepancy determination system 102, but the process 300 may also, or instead, be performed in other similar and/or different environments by other similar and/or different systems.

At 302, image source data may be determined (e.g., received, retrieved, acquired, etc.). Image source data may include, but is not limited to, an image of any type and/or image data representing an image of any type. For example, the image source data may include an X-ray, an MRI image, a CT scan image, a CAT scan image, an ultrasound image, a histology image, an OCT image, a fundus image, a histology image, a pathology image, a histopathology image, and/or any other form of digital and/or analog image.

At 304, text source data associated with the image source data determined at 302 may be determined (e.g., received, retrieved, acquired, etc.). Text source data may include, but is not limited to, descriptive text provided by a user that has visually analyzed an image or image data associated with the image source data of 302. For example, the text source data may be textual data input by a radiologist analyzing an X-ray or other type of medical image, an engineer analyzing an image of a mechanical component generated using a computer vision system, a technician or doctor analyzing an image of an implanted medical device, etc. Such textual data may be a textual description of one or more conditions and/or parameters identified by the analyzing user.

At 306, the image source data of 302 may be used as input to an image processing model that may be executed to generate one or more prediction values as output. The image processing model may include one or more machine-learned models and/or neural networks trained to determine values for a set of conditions and/or parameters based on image input. For example, the image processing model may be configured to determine predicted values for a predetermined set of medical conditions, demographic parameters, and image parameters based on an image or image data. The image processing model may be executed by an image processing component that may generate predicted values based on the output of the image processing model, which may include simply providing the output of the image processing model as predicted values and/or modifying and/or further processing the output of the image processing model to generate the predicted values (e.g., as described herein).

At 308, the text source data of 304 may be used as input to a text processing model that may be executed to generate one or more prediction values as output. The text processing model may include one or more machine-learned models (e.g., one or more natural language processing (NLP) models) and/or neural networks trained to determine values for a set of conditions and/or parameters based on textual data input. For example, the text processing model may be configured to determine predicted values for a predetermined set of medical conditions, demographic parameters, and image parameters based on textual data. The text processing model may be executed by a text processing component that may generate predicted values based on the output of the text processing model, which may include simply providing the output of the text processing model as predicted values and/or modifying and/or further processing the output of the text processing model to generate the predicted values (e.g., as described herein).

At 310, the predicted values generated at 306 may be compared to corresponding predicted values generated at 308 to determine discrepancies. For example, a predicted value generated for a particular condition or parameter at 306 may be compared to a predicted value generated for the same particular condition or parameter at 308 to determine if there is a difference between such values. This discrepancy determination operation may be performed for the predicted values generated for the individual conditions and/or parameters in the set of conditions and/or parameters (e.g., the predetermined set of medical conditions, demographic parameters, and image parameters). In examples, differences of any type may be considered discrepancies.

At 312, the system may determine whether a determined discrepancy is sufficiently significant. As described herein, this sufficiency of significance may be based on a variety of factors. In examples, any difference between two predicted values of a same condition or parameter may be considered sufficiently significant. Alternatively or additionally, a difference between two predicted values of a same condition or parameter that is equal to or greater than a threshold value may be considered sufficiently significant. Other criteria for determining significance may be utilized in addition to or instead of absolute difference and threshold amounts of difference.

If, at 312, a determined discrepancy for a particular condition or parameter is determined to be insufficiently significant, at 320, data may be stored indicating the discrepancy determination, the significance determination, and/or other related data. In examples, the source data of 302 and 304 may be supplemented or augmented with the discrepancy determination results associated with such source data. This augmentation data may indicate that the values for the particular condition or parameter are sufficiently congruent. Alternatively or additional, if a determined discrepancy is determined to be insufficiently significant, no action may be taken at 320.

If, at 312, a determined discrepancy is determined to be sufficiently significant, at 314 the system may determine the relevance of the determined discrepancy. As described herein, the relevance of a determined discrepancy may be based on one or more factors that may be used to determine whether the determined discrepancy should be indicated (e.g., to a user) as a discrepancy. As described herein, one or more parameters and/or conditions in a set may be configured at a discrepancy determination system as relevant and/or irrelevant (e.g., as configured by a user, according to attributes of the parameter or condition, etc.). The system may determine whether a condition or parameter associated with the determined discrepancy is indicated as a relevant condition or parameter at 314.

At 316, if the determined discrepancy for a particular condition or parameter is determined to be not relevant, data may be stored indicating the discrepancy determination, the relevance determination, and/or other related data. In examples, the source data of 302 and 304 may be supplemented or augmented with the discrepancy determination results associated with such source data. This augmentation data may indicate that the determined discrepancy was not relevant. Alternatively or additionally, if a determined discrepancy is determined not to be relevant, no action may be taken at 320.

If, at 316, the determined discrepancy for a particular condition or parameter is determined to be relevant, at 318 the discrepancy determination system may generate a discrepancy report and/or alert indicating the determined discrepancy (e.g., to a user and/or for storage at a data store). For example, the system may transmit an individual alert (e.g., as an email, present as an interface element, etc.) for the determined discrepancy. Alternatively or additionally, the system may ass the determined discrepancy to a discrepancy report alert (e.g., as an email, present as an interface element, etc.) that may include or indicate one or more determined discrepancies, for example, as a summary of the results of processing a batch of images and associated data by a discrepancy determination system.

FIG. 4A illustrates an example 401 of prediction data and an exemplary interface on which such data may be presented. In various examples, the processing and generation of data illustrated in the figure may be performed, at least in part, by a discrepancy determination system, such as the discrepancy determination system 102 of FIG. 1. For example, image prediction data 410 may correspond to image prediction data 128 of FIG. 1, and may be generated using an image prediction generation component, such as the image prediction generation component 116 of FIG. 1, that may include one or more ML models and/or neural networks, such as the image processing model 118 of FIG. 1. The image prediction data 410 may include output data generated by an image processing model executed using an image as input.

In examples, the image prediction generation component may be configured to determine predicted values for a set of conditions and/or parameters using an image. For example, the image prediction generation component may be configured to determine condition data 420 that includes predicted values for conditions 421-425, demographic data 430 that includes predicted values for demographic parameters 431-433, and image metadata 440 that includes predicted values for image parameters 441-443. In a demonstrative medical example, the conditions of the condition data 420 may include any one or more medical conditions, such as atelectasis, consolidation, edema, emphysema, fibrosis, effusion, pleural thickening, cardiomegaly, mass, hernia, lung opacity, and enlarged cardiomedia. In this example, the parameters of the demographic data 430 may include any one or more demographic parameters that may be associated with a patient or human subject, such as sex, race, age, gender, behavioral attribute(s), environmental attribute(s), social determinant(s), etc. Continuing with this medical example, the parameters of the image data 440 may include any one or more image parameters that may be associated with a scan or image of a patient or human subject, such as patient position, imaging device or system (e.g., camera) data (e.g., position, focal length, model, make, etc.), image data and/or metadata (e.g., resolution, time/date of capture, location, etc.), etc. Such image parameters may include or be represented as DICOM tags, DICOM header data, and/or other DICOM data.

The predicted values and associated data of the image prediction data 410 may be presented to a user in a variety of forms. For example, the predicted values may be presented as interface elements on an interface, as shown here for the demographic data 430 (e.g., "43" for demographic parameter 431, "X" for demographic parameter 432, and "Y" for demographic parameter 433) and the image metadata 440 (e.g., "Frontal" for image parameter 441, "I" for image parameter 442, and "J" for image parameter 443). The predicted values for the various conditions of the condition data 420 are also shown here as risk values 428.

One or more graphical representations of predicted values may also be presented to a user as one or more interface elements. For example, the predicted condition values of the condition data 420 may be represented as graphical elements 426 that indicate the predicted value along a spectrum or scale of possible values.

In examples, the predicted values illustrated as the image condition data 410 may also, or instead, be stored for use in discrepancy determination operations. For instance, no interfaces may be generated to present predicted values generated for the individual modalities used in discrepancy determination operations, but rather such data may be stored for performing the discrepancy determination operations.

FIG. 4B illustrates an example 402 of prediction data and an exemplary interface on which such data may be presented. In various examples, the processing and generation of data illustrated in the figure may be performed, at least in part, by a discrepancy determination system, such as the discrepancy determination system 102 of FIG. 1. For example, text prediction data 450 may correspond to text prediction data 130 of FIG. 1, and may be generated using a text prediction generation component, such as the text prediction generation component 120 of FIG. 1, that may include one or more ML models and/or neural networks, such as the text processing model 122 of FIG. 1. The text prediction data 450 may include output data generated by a text processing model executed using a textual data associated with an image as input. In this example, the textual data may be associated with the image processed to generate the exemplary prediction values described in regard to FIG. 4A.

In examples, the text prediction generation component may be configured to determine predicted values for a set of conditions and/or parameters using textual data associated with an image, such as the image processed to generate the predicted values described in regard to FIG. 4A. For example, the text prediction generation component may be configured to determine condition data 460 that includes predicted values for the conditions 421-425, predicted values for the demographic data 470 that includes the demographic parameters 431-433, and predicted values for the image metadata 480 that includes image parameters 441-443. In this example, the conditions of the condition data 460 may be the same conditions as those of the condition data 420 described in regard to FIG. 4A, the demographic parameters of the demographic data 470 may be the same parameters as those of demographic data 430 described in regard to FIG. 4A, and the image parameters of the image metadata 480 may be the same parameters as those of image metadata 440 described in regard to FIG. 4A. For example, the text prediction generation component may be configured to determine predicted DICOM data and/or parameter values for comparison to the image metadata 440 that may accompany an image. Continuing the demonstrative medical example initiated above, the conditions of the condition data 460 may include any one or more of the medical conditions described in regard to FIG. 4A, the demographic data 470 may include any one or more of the demographic parameters described in regard to FIG. 4A, and the image metadata 480 may include any one or more image parameters described in regard to FIG. 4A.

The predicted values and associated data of the text prediction data 450 may be presented to a user in a variety of forms, as with the example of FIG. 4A, including predicted values presented as interface elements on an interface, as shown here for the demographic data 470 (e.g., "13" for demographic parameter 431, "X" for demographic parameter 432, and "Y" for demographic parameter 433) and the image metadata 480 (e.g., "Side" for image parameter 441, "Q" for image parameter 442, and "J" for image parameter

443). The predicted values for the various conditions of the condition data 460 are also shown here as risk values 468.

As noted, one or more graphical representations of predicted values may also be presented to a user as one or more interface elements. For example, the predicted condition values of the condition data 460 may be represented as graphical elements 466 that indicate the predicted value along a spectrum or scale of possible values.

Here again, the predicted values illustrated as the text condition data 450 may also, or instead, be stored for use in discrepancy determination operations. For instance, no interfaces may be generated to present predicted values generated for the individual modalities used in discrepancy determination operations, but rather such data may be stored for performing the discrepancy determination operations.

Figure 5:
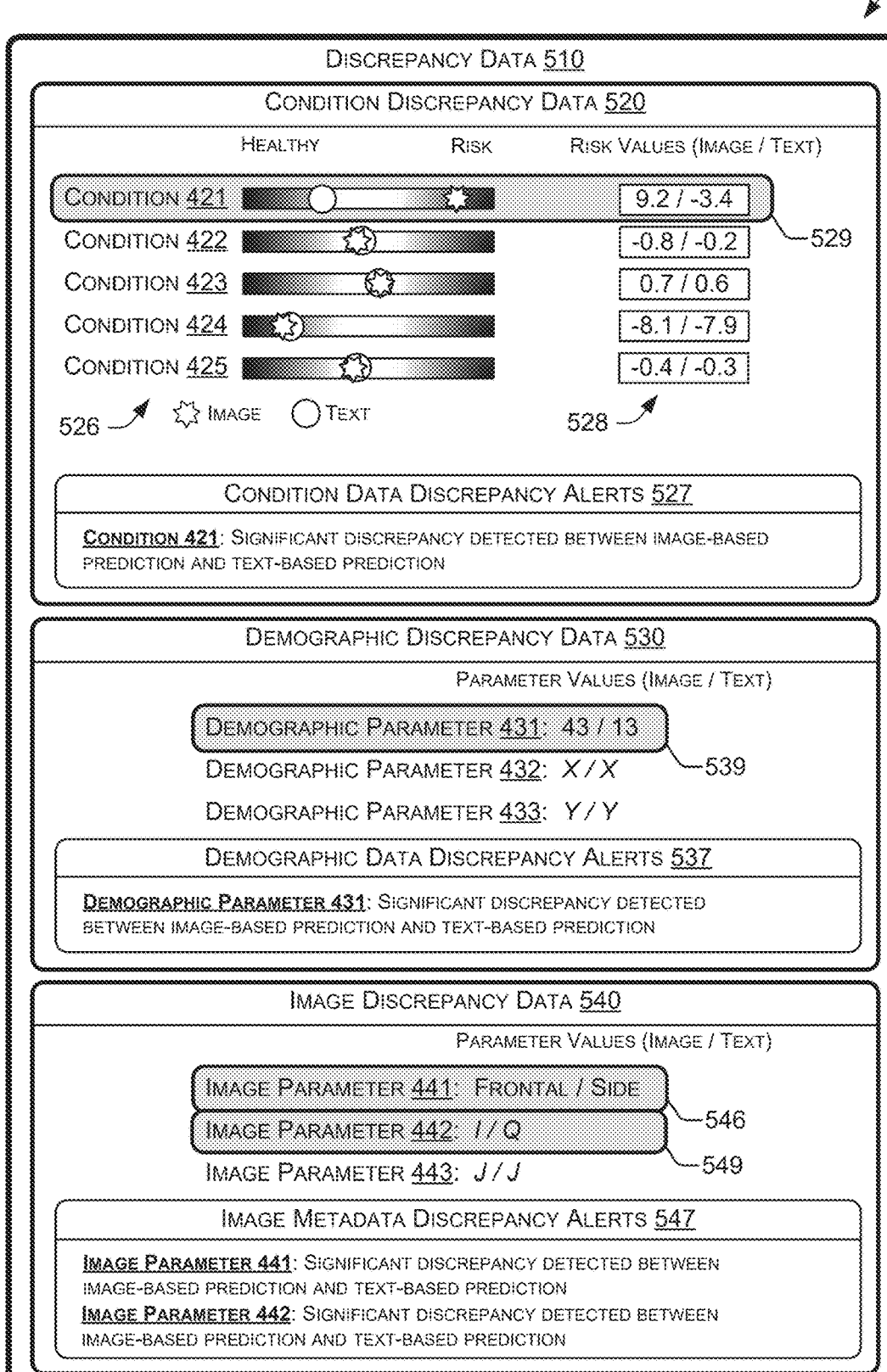
FIG. 5 illustrates a block diagram representing exemplary discrepancy data that may be received, processed, and/or generated by a system implementing a discrepancy detection framework.

FIG. 5 illustrates an example 501 of discrepancy data and an exemplary interface on which such data may be presented. In various examples, the determination of the discrepancy data illustrated in the figure may be performed, at least in part, by a discrepancy determination system, such as the discrepancy determination system 102 of FIG. 1. For example, discrepancy data 510 may correspond to discrepancy data 136 of FIG. 1, and may be generated using a discrepancy determination component, such as the discrepancy determination component 134 of FIG. 1. The text prediction data 450 may input data generated by an image prediction generation component and/or a text prediction generation component as described herein (e.g., in regard to FIGS. 4A and 4B above).

In examples, the discrepancy determination system component may be configured to determine discrepancies between predicted values generated for a set of conditions and/or parameters using modality data associated with an image, such as the image and data processed to generate the predicted values described in regard to FIGS. 4A and 4B. For example, the discrepancy determination system may be configured to determine condition discrepancy data 510 that includes comparisons and discrepancies between predicted values for the conditions 421-425, demographic discrepancy data 530 that includes comparisons and discrepancies between predicted values for the demographic parameters 431-433, and image discrepancy data 540 that includes comparisons and discrepancies between predicted values for the image parameters 441-443. In this examples, the comparisons performed to determine discrepancies may be comparisons of the predicted values of the condition data 420 described in regard to FIG. 4A and the predicted values of the condition data 460 described in regard to FIG. 4B, comparisons of the predicted values of the demographic data 430 described in regard to FIG. 4A and the predicted values of the demographic data 470 described in regard to FIG. 4B, and comparisons of the predicted values of the image metadata 440 described in regard to FIG. 4A and the predicted values of the image metadata 480 described in regard to FIG. 4B.

The discrepancy data 510 may be presented to a user in a variety of forms, similar to the examples of FIGS. 4A and 4B, including predicted values for the compared modalities presented as interface elements on an interface, as shown here for the demographic discrepancy data 530 (e.g., "43/13" for demographic parameter 431, "X/X" for demographic parameter 432, and "Y/Y" for demographic parameter 433) and the image discrepancy data 540 (e.g., "Frontal/Side" for image parameter 441, "I/Q" for image parameter 442, and "J/J" for image parameter 443). The compared predicted values for the various conditions 421-425 are also shown here as compared risk values 528.

One or more graphical representations of compared predicted values may also be presented to a user as one or more interface elements. For example, the compared predicted condition values for the conditions 421-425 may be represented as graphical elements 526 that indicate the predicted value for each modality along a spectrum or scale of possible values. This may facilitate easily representing those comparisons that are associated with a (e.g., significant) discrepancy.

Indications of various determined discrepancies may be included in the discrepancy data 510 and/or indicated on an interface presenting such data. For example, the condition data discrepancy alerts 527 interface element may include a textual indication that may describe a determined condition discrepancy (e.g., with regard to condition 421 in this example). A graphical representation 529 of this discrepancy may also, or instead, be included and/or indicated in the condition discrepancy data 520.

Similarly, the demographic discrepancy data 530 may include a textual indication, such as a demographic data discrepancy alerts 537 interface element, that may describe a determined demographic data discrepancy (e.g., with regard to demographic parameter 431 in this example). A graphical representation 539 of this discrepancy may also, or instead, be included and/or indicated in the demographic discrepancy data 530.

Likewise, the image discrepancy data 540 may include textual indications, such as those represented in an image data discrepancy alerts 547 interface element, that may describe determined image data discrepancies (e.g., with regard to image parameters 441 and 442 in this example). Graphical representations 546 and 549 of these discrepancies may also, or instead, be included and/or indicated in the image discrepancy data 540.

As with the data of FIGS. 4A and 4B, Here again, the data illustrated as discrepancy data 510 may also, or instead, be stored for other uses and future reference. For instance, no interfaces may be generated to present discrepancy determination data, but rather such data may be stored for generating the discrepancy determination alerts and operations and/or for operations.

Figure 6:
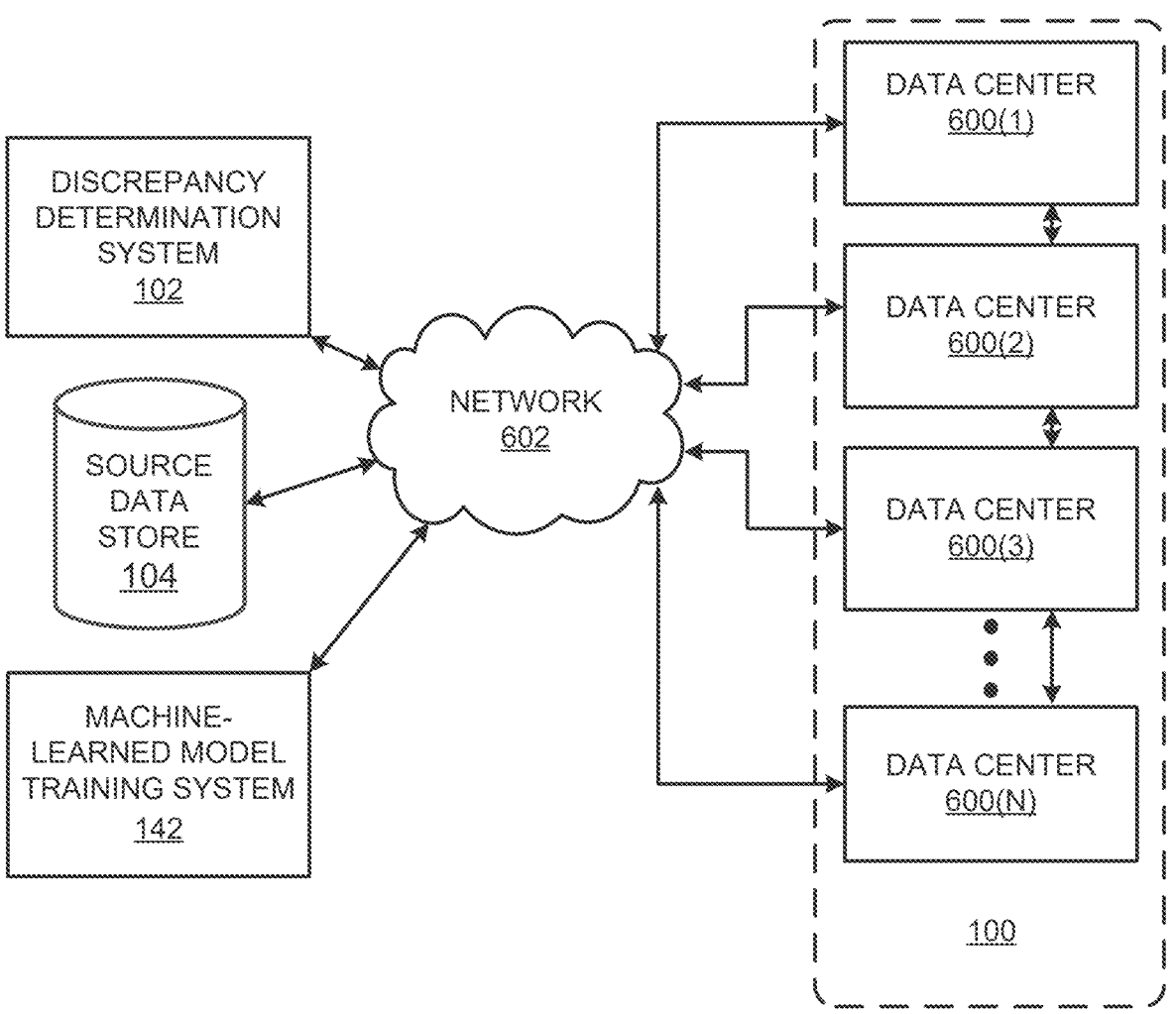
FIG. 6 is a system and network diagram that shows an illustrative operating environment that includes a system that can be configured to implement aspects of the functionality described herein.

FIG. 6 is a system and network diagram that shows an illustrative operating environment that includes a discrepancy determination system 102, a source data store 104, and a machine-learned model training system 142 that can be configured to implement aspects of the functionality described herein. The systems 102, 104, and 142 can each execute and/or implement various types of computing and network services, such as data storage and data processing, and/or utilize various computing resources of various types of systems on a permanent or an as-needed basis. Among other types of functionality, the computing resources utilized and/or implemented by the systems 102, 104, and 142, or by a larger system of which one or more of these systems may be a part, can be utilized to implement the various discrepancy determination operations and model training operations described herein. One or more of the systems 102, 104, and 142 may be part of a larger system that provides additional computing resources that include, without limitation, data storage resources, data processing resources, such as virtual machine (VM) instances, networking resources, data communication resources, network services, and other types of resources.

Each type of computing resource utilized and/or implemented at the systems 102, 104, and 142, or by a larger system of which one or more of these systems may be a part, can be general-purpose or can be available in a number of specific configurations. For example, data processing resources can be implemented as physical computers or VM instances in a number of different configurations. The VM instances can be configured to execute applications, including web servers, application servers, media servers, database servers, some or all of the discrepancy determination operations and/or model training operations described above, and/or other types of programs. Data storage resources can include file storage devices, block storage devices, and the like. The systems 102, 104, and 142, or a larger system of which one or more of these systems may be a part, can also be configured to perform other types of operations and/or utilize and/or implement other computing resources not mentioned specifically herein.

The computing resources utilized and/or implement by systems 102, 104, and 142, or a larger system of which one or more of these systems may be a part, may be enabled in one implementation by one or more data centers 600(1), 600(2), 600(3), . . . , 600(N) that may be configured in (partially or wholly) and/or communicative connected to the environment 100. The data centers are facilities utilized to house and operate computer systems and associated components. The data centers typically include redundant and backup power, communications, cooling, and security systems. The data centers can also be located in geographically disparate locations. One illustrative configuration for a data center that can be utilized to implement the technologies disclosed herein will be described below with regard to FIG. 7.

The users of the system can access the computing resources, such as systems 102, 104, and 142, and/or any of the computing resources in the environment 100, provided by the system over a network 602, which can be a wide area communication network ("WAN"), such as the Internet, an intranet, an Internet service provider ("ISP") network, or a combination of such networks. For example, and without limitation, a computing device (e.g., the discrepancy determination system 102) operated by a user of the system can be utilized to access the system by way of the network 602. It should be appreciated that a local-area network ("LAN"), the Internet, or any other networking topology known in the art that connects the data centers to remote users and other users can be utilized. It should also be appreciated that combinations of such networks can also be utilized.

Figure 7:
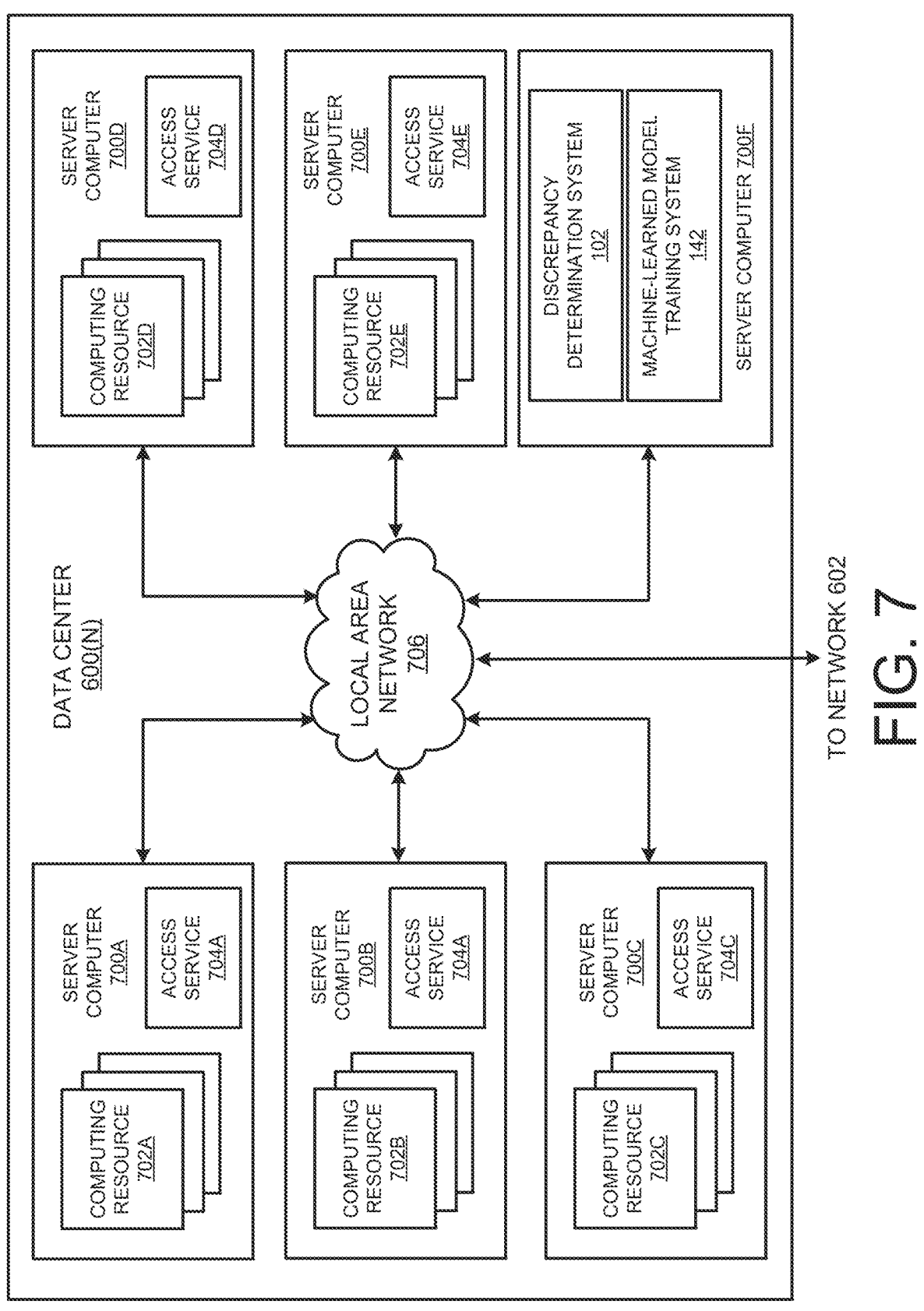
FIG. 7 is a computing system diagram illustrating a configuration for a data center that can be utilized to implement aspects of the technologies disclosed herein.

FIG. 7 is a computing system diagram that illustrates one configuration for a data center 600(N) that can be utilized to implement the systems 102, 104, and/or 142, as described above in FIGS. 1-5 and/or any other discrepancy determination system and/or model training system disclosed herein. The example data center 600(N) shown in FIG. 7 includes several server computers 700A-700E (collectively 700) for providing the computing resources 702A-702E (collectively 702), respectively.

The server computers 700 can be standard tower, rackmount, or blade server computers configured appropriately for providing the various computing resources described herein (illustrated in FIG. 7 as the computing resources 702A-702E). As mentioned above, the computing resources 702 may be utilized and/or configured at one or more of systems 102, 104, and 142, or a larger system of which these systems may be a part, and can include, without limitation, analytics applications, data storage resources, data processing resources such as VM instances or hardware computing systems, database resources, networking resources, model execution resources, model training resources, and others. Some of the servers 700 can also be configured to execute access services 704A-704E (collectively 704) capable of instantiating, providing and/or managing the computing resources 702, some of which are described in detail herein.

The data center 600(N) shown in FIG. 7 also includes a server computer 700F that can execute some or all of the software components described above. For example, and without limitation, the server computer 700F can be configured to execute one or more of the discrepancy determination system 102, the source data store 104, the machine-learned model training system 142, and/or one or more components associated therewith. The server computer 700F can also be configured to execute other components and/or to store data for providing some or all of the functionality described herein. In this regard, it should be appreciated that components or different instances of one or more of the systems 102, 104, and 142 can execute on many other physical or virtual servers in the data centers 600 in various configurations.

In the example data center 600(N) shown in FIG. 7, an appropriate LAN 706 is also utilized to interconnect the server computers 700A-700F. The LAN 706 is also connected to the network 602 illustrated in FIG. 6. It should be appreciated that the configuration of the network topology described herein has been greatly simplified and that many more computing systems, software components, networks, and networking devices can be utilized to interconnect the various computing systems disclosed herein and to provide the functionality described above.

Appropriate load balancing devices or other types of network infrastructure components can also be utilized for balancing a load between each of the data centers 600(1)-(N), between each of the server computers 700A-700F in each data center 600, and, potentially, between computing resources 702 in each of the data centers 600. It should be appreciated that the configuration of the data center 600 described with reference to FIG. 7 is merely illustrative and that other implementations can be utilized.

Figure 8:
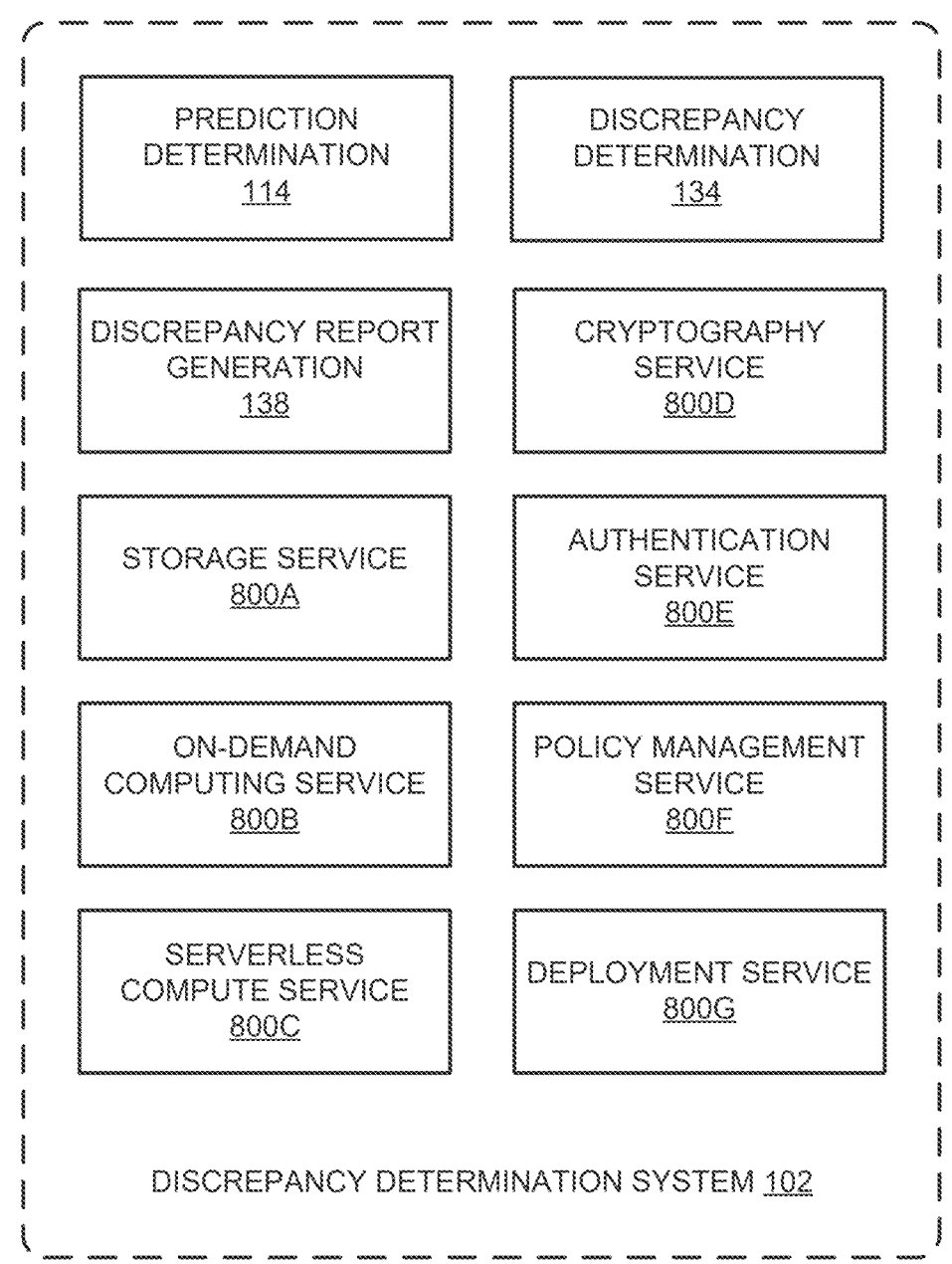
FIG. 8 is a network services diagram that shows aspects of several services that can be provided by and utilized within a system, or a larger system of which the system is a part, which is configured to implement the various technologies disclosed herein.

FIG. 8 is a system services diagram that shows aspects of several services that can be provided by and utilized within the discrepancy determination system 102 and/or a larger system of which this system may be a part, which is configured to implement the various technologies disclosed herein. In particular, and as discussed above, this system, or a larger system of which this system may be a part, can provide a variety of services to users and other users including, but not limited to, discrepancy determination services performed by a prediction determination component 114, a discrepancy determination component 134, discrepancy repost generation component 138, and/or one or more computing instances performing one or more functions thereof; a storage service 800A; an on-demand computing service 800B; a serverless compute service 800C; a cryptography service 800D; an authentication service 800E; a policy management service 800F; and a deployment service 800G. The system, or a larger system of which the system is a part, can also provide other types of computing services, some of which are described below.

It is also noted that not all configurations described include the services shown in FIG. 8 and that additional services can be provided in addition to, or as an alternative to, the services explicitly described herein. Each of the systems and services shown in FIG. 8 can also expose web service interfaces that enable a caller to submit appropriately configured API calls to the various services through web service requests. The various web services can also expose GUIs, command line interfaces ("CLIs"), and/or other types of interfaces for accessing the functionality that they provide. In addition, each of the services can include service interfaces that enable the services to access each other. Additional details regarding some of the services shown in FIG. 8 will now be provided.

The storage service 800A can be a network-based storage service that stores data obtained from users of the system and/or from computing resources in the system, or a larger system of which the system is a part. The data stored by the storage service 800A can be obtained from computing devices of users. The data stored by the storage service 800A may also be activity data logged to the storage system 800A that may be functioning as a logging system or service.

The on-demand computing service 800B can be a collection of computing resources configured to instantiate VM instances and to provide other types of computing resources on demand. For example, a user of the system, or a larger system of which the system is a part, can interact with the on-demand computing service 800B (via appropriately configured and authenticated API calls, for example) to provision and operate VM instances that are instantiated on physical computing devices hosted and operated by the system, or a larger system of which the system is a part. The VM instances can be used for various purposes, such as to operate as servers supporting the network services described herein, a web site, to operate business applications or, generally, to serve as computing resources for the user.

Other applications for the VM instances can be to support database applications, electronic commerce applications, business applications and/or other applications. Although the on-demand computing service 800B is shown in FIG. 8, any other computer system or computer system service can be utilized in the system, or a larger system of which the system is a part, to implement the functionality disclosed herein, such as a computer system or computer system service that does not employ virtualization and instead provisions computing resources on dedicated or shared computers/servers and/or other physical devices.

The serverless compute service 800C is a network service that allows users to execute code (which might be referred to herein as a "function") without provisioning or managing server computers in the system, or a larger system of which the system is a part. Rather, the serverless compute service 800C can automatically run code in response to the occurrence of events. The code that is executed can be stored by the storage service 800A or in another network accessible location.

In this regard, it is to be appreciated that the term "serverless compute service" as used herein is not intended to infer that servers are not utilized to execute the program code, but rather that the serverless compute service 800C enables code to be executed without requiring a user to provision or manage server computers. The serverless compute service 800C executes program code only when needed, and only utilizes the resources necessary to execute the code. In some configurations, the user or entity requesting execution of the code might be charged only for the amount of time required for each execution of their program code.

The system, or a larger system of which the system is a part, can also include a cryptography service 800D. The cryptography service 800D can utilize storage services of the system, or a larger system of which the system is a part, such as the storage service 800A, to store encryption keys in encrypted form, whereby the keys can be usable to decrypt user keys accessible only to particular devices of the cryptography service 800D. The cryptography service 800D can also provide other types of functionality not specifically mentioned herein.

The system, or a larger system of which the system is a part, in various configurations, also includes an authentication service 800E and a policy management service 800F. The authentication service 800E, in one example, is a computer system (i.e., collection of computing resources 800B) configured to perform operations involved in authentication of users or customers. For instance, one of the services shown in FIG. 8 can provide information from a user or customer to the authentication service 800E to receive information in return that indicates whether or not the requests submitted by the user or the customer are authentic.

The policy management service 800F, in one example, is a network service configured to manage policies on behalf of users or customers of the system, or a larger system of which the system is a part. The policy management service 800F can include an interface (e.g., API or GUI) that enables customers to submit requests related to the management of policy, such as a security policy. Such requests can, for instance, be requests to add, delete, change, or otherwise modify policy for a customer, service, or system, or for other administrative actions, such as providing an inventory of existing policies and the like.

The system, or a larger system of which the system is a part, can additionally maintain other network services based, at least in part, on the needs of its customers. For instance, the system, or a larger system of which the system is a part, can maintain a deployment service 800G for deploying program code in some configurations. The deployment service 800G provides functionality for deploying program code, such as to virtual or physical hosts provided by the on-demand computing service 800B. Other services include, but are not limited to, database services, object-level archival data storage services, and services that manage, monitor, interact with, or support other services. The system, or a larger system of which the system is a part, can also be configured with other network services not specifically mentioned herein in other configurations.

Figure 9:
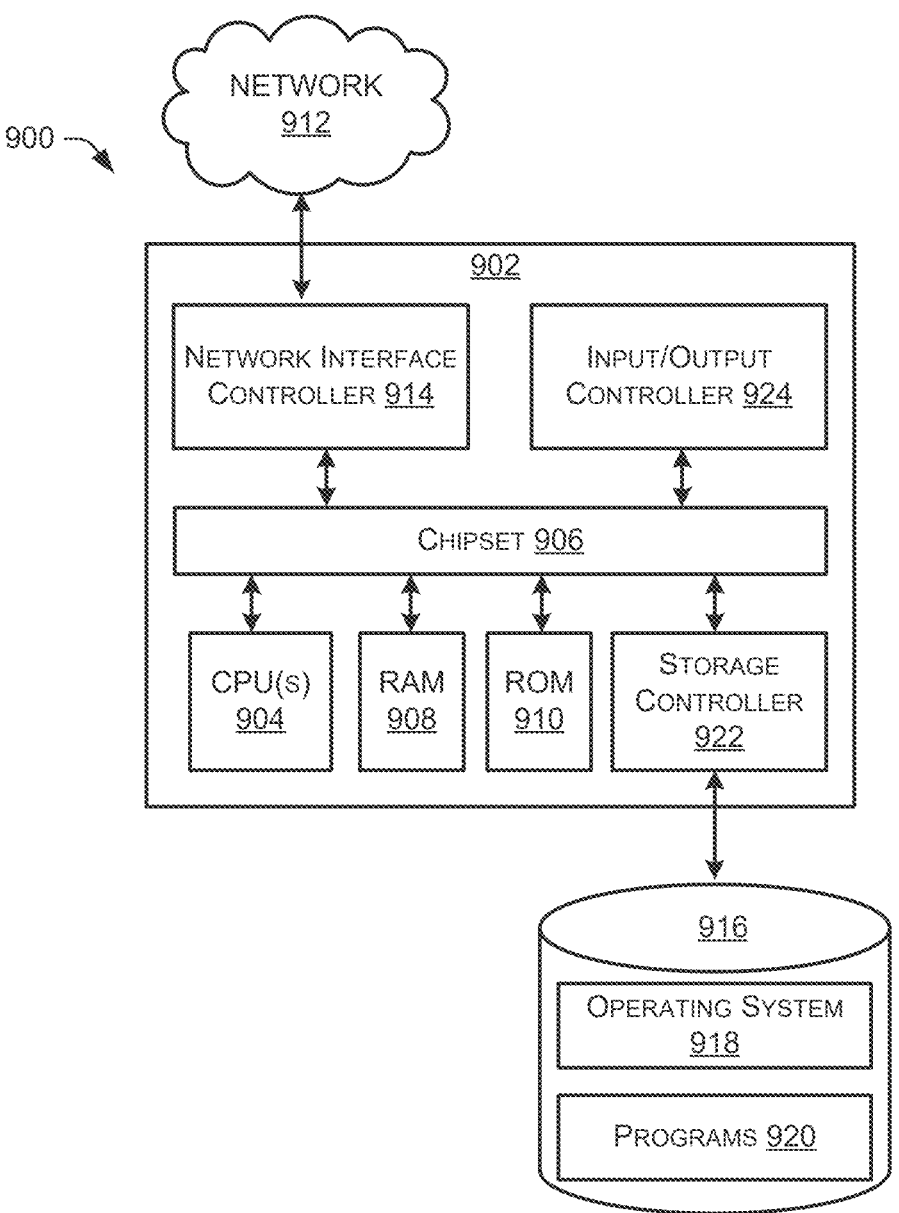
FIG. 9 is a computer architecture diagram showing an illustrative computer hardware architecture for implementing a computing device that can be utilized to implement aspects of the various technologies presented herein.

FIG. 9 shows an example computer architecture for a computer 900 capable of executing program components for implementing the functionality described above. The computer architecture shown in FIG. 9 illustrates a conventional server computer, workstation, desktop computer, laptop, tablet, network appliance, e-reader, smartphone, or other computing device, and can be utilized to execute any of the software components presented herein. The computer 900 may represent architecture for a PII detection system, a model training system, and/or other systems and components described herein.

The computer 900 includes a baseboard 902, or "motherboard," which may be one or more printed circuit boards to which a multitude of components and/or devices may be connected by way of a system bus and/or other electrical communication paths. In one illustrative configuration, one or more central processing units ("CPUs") 904 operate in conjunction with a chipset 906. The CPUs 904 can be standard programmable processors that perform arithmetic and logical operations necessary for the operation of the computer 900.

The CPUs 904 perform operations by transitioning from one discrete, physical state to the next through the manipulation of switching elements that differentiate between and change these states. Switching elements can generally include electronic circuits that maintain one of two binary states, such as flip-flops, and electronic circuits that provide an output state based on the logical combination of the states of one or more other switching elements, such as logic gates.

These basic switching elements can be combined to create more complex logic circuits, including registers, adders-subtractors, arithmetic logic units, floating-point units, and the like.

The chipset 906 provides an interface between the CPUs 904 and the remainder of the components and devices on the baseboard 902. The chipset 906 can provide an interface to a RAM 908, used as the main memory in the computer 900. The chipset 906 can further provide an interface to a computer-readable storage medium such as a read-only memory ("ROM") 910 or non-volatile RAM ("NVRAM") for storing basic routines that help to startup the computer 900 and to transfer information between the various components and devices. The ROM 910 or NVRAM can also store other software components necessary for the operation of the computer 900 in accordance with the configurations described herein.

The computer 900 can operate in a networked environment using logical connections to remote computing devices and computer systems through a network, such as the network 912. The chipset 906 can include functionality for providing network connectivity through a NIC 914, such as a gigabit Ethernet adapter. The NIC 914 is capable of connecting the computer 900 to other computing devices over the network 912. It should be appreciated that multiple NICs 914 can be present in the computer 900, connecting the computer to other types of networks and remote computer systems.

The computer 900 can be connected to a mass storage device 916 that provides non-volatile storage for the computer. The mass storage device 916 can store an operating system 918, programs 920, and data, which have been described in greater detail herein. The mass storage device 916 can be connected to the computer 900 through a storage controller 922 connected to the chipset 906. The mass storage device 916 can consist of one or more physical storage units. The storage controller 922 can interface with the physical storage units through a serial attached SCSI ("SAS") interface, a serial advanced technology attachment ("SATA") interface, a fiber channel ("FC") interface, or other type of interface for physically connecting and transferring data between computers and physical storage units.

The computer 900 can store data on the mass storage device 916 by transforming the physical state of the physical storage units to reflect the information being stored. The specific transformation of physical state can depend on various factors, in different implementations of this description. Examples of such factors can include, but are not limited to, the technology used to implement the physical storage units, whether the mass storage device 916 is characterized as primary or secondary storage, and the like.

For example, the computer 900 can store information to the mass storage device 916 by issuing instructions through the storage controller 922 to alter the magnetic characteristics of a particular location within a magnetic disk drive unit, the reflective or refractive characteristics of a particular location in an optical storage unit, or the electrical characteristics of a particular capacitor, transistor, or other discrete component in a solid-state storage unit. Other transformations of physical media are possible without departing from the scope and spirit of the present description, with the foregoing examples provided only to facilitate this description. The computer 900 can further read information from the mass storage device 916 by detecting the physical states or characteristics of one or more particular locations within the physical storage units.

In addition to the mass storage device 916 described above, the computer 900 can have access to other computer-readable storage media to store and retrieve information, such as program modules, data structures, or other data. It should be appreciated by those skilled in the art that computer-readable storage media is any available media that provides for the non-transitory storage of data and that can be accessed by the computer 900.

By way of example, and not limitation, computer-readable storage media can include volatile and non-volatile, removable and non-removable media implemented in any method or technology. Computer-readable storage media includes, but is not limited to, RAM, ROM, erasable programmable ROM ("EPROM"), electrically-erasable programmable ROM ("EEPROM"), flash memory or other solid-state memory technology, compact disc ROM ("CD-ROM"), digital versatile disk ("DVD"), high definition DVD ("HD-DVD"), BLU-RAY, or other optical storage, magnetic cassettes, magnetic tape, magnetic disk storage or other magnetic storage devices, or any other medium that can be used to store the desired information in a non-transitory fashion.

As mentioned above, the mass storage device 916 can store an operating system 918 utilized to control the operation of the computer 900. According to one configuration, the operating system comprises the LINUX operating system or one of its variants such as, but not limited to, UBUNTU, DEBIAN, and CENTOS. According to another configuration, the operating system comprises the WINDOWS SERVER operating system from MICROSOFT Corporation. According to further configurations, the operating system can comprise the UNIX operating system or one of its variants. It should be appreciated that other operating systems can also be utilized. The mass storage device 916 can store other system or application programs and data utilized by the computer 900.

In one configuration, the mass storage device 916 or other computer-readable storage media is encoded with computer-executable instructions which, when loaded into the computer 900, transform the computer from a general-purpose computing system into a special-purpose computer capable of implementing the configurations described herein. These computer-executable instructions transform the computer 900 by specifying how the CPUs 904 transition between states, as described above. According to one configuration, the computer 900 has access to computer-readable storage media storing computer-executable instructions which, when executed by the computer 900, perform the various processes described above. The computer 900 can also include computer-readable storage media for performing any of the other computer-implemented operations described herein.

The computer 900 can also include one or more input/output controllers 924 for receiving and processing input from a number of input devices, such as a keyboard, a mouse, a touchpad, a touch screen, an electronic stylus, or other type of input device. Similarly, an input/output controller 924 can provide output to a display, such as a computer monitor, a flat-panel display, a digital projector, a printer, or other type of output device. It will be appreciated that the computer 900 might not include all of the components shown in FIG. 9, can include other components that are not explicitly shown in FIG. 9, or can utilize an architecture completely different than that shown in FIG. 9.

Based on the foregoing, it should be appreciated that technologies for determining discrepancies between predicted values generated based on various modalities have been disclosed herein. Moreover, although the subject matter presented herein has been described in language specific to computer structural features, methodological acts, and computer readable media, it is to be understood that the invention defined in the appended claims is not necessarily limited to the specific features, acts, or media described herein. Rather, the specific features, acts, and media are disclosed as example forms of implementing the claims.

The subject matter described above is provided by way of illustration only and should not be construed as limiting. Furthermore, the claimed subject matter is not limited to implementations that solve any or all disadvantages noted in any part of this disclosure. Various modifications and changes can be made to the subject matter described herein without following the example configurations and applications illustrated and described, and without departing from the true spirit and scope of the present invention, which is set forth in the following claims.

What is claimed is:

1. A method comprising:

receiving, at a discrepancy determination system, source data comprising an image representing a portion of a human subject and textual data associated with the image;

executing, by the discrepancy determination system and using the image as first input, a machine-learned image processing model to determine first values for a set of medical conditions represented in the image;

executing, by the discrepancy determination system and using the textual data as second input, a machine-learned text processing model to determine second values for the set of medical conditions represented in the image;

determining, by the discrepancy determination system, a first discrepancy value based on a difference between a first value of the first values associated with a medical condition of the set of medical conditions and a corresponding second value of the second values associated with the medical condition of the set of medical conditions;

determining, by the discrepancy determination system, that the discrepancy value meets or exceeds a first discrepancy threshold;

executing, by the discrepancy determination system and using the image data as the first input, the machine-learned image processing model to determine third values for the set of medical conditions represented in the image;

executing, by the discrepancy determination system and using the image data as the first input, the machine-learned image processing model to determine fourth values for the set of medical conditions represented in the image;

determining, by the discrepancy determination system, a second discrepancy value based on a difference between a third value of the third values associated with the medical condition of the set of medical conditions and a corresponding fourth value of the fourth values associated with the medical condition of the set of medical conditions;

determining, by the discrepancy determination system, that the second discrepancy value is below a second discrepancy threshold; and transmitting, by the discrepancy determination system to a computing device for presentation on an interface and based on determining that the first discrepancy value meets or exceeds the first discrepancy threshold, an indication of the medical condition of the set of medical conditions and the first discrepancy value but excluding the second discrepancy value from the indication based at least in part on determining that the second discrepancy is below the second discrepancy threshold.

2. The method of claim 1, wherein the image comprises one of an X-ray, a magnetic resonance imaging (MRI) image, a computed tomography (CT) scan image, a computed axial tomography (CAT) scan image, an ultrasound image, a histology image, optical coherence tomography (OCT) image, or a fundus image.

3. The method of claim 1 wherein the first value and the second value each indicate one of:

a likelihood of a presence of the medical condition; or a risk associated with the medical condition.

4. A method comprising:

receiving, by one or more computing devices, first data of a first modality associated with an image and second data of a second modality associated with the image;

executing, by the one or more computing devices and using the first data as first input, at least one of a first prediction generation component or a second prediction generation component to determine a first value for a first parameter of the image;

executing, by the one or more computing devices and using the second data as second input, at least one of the first prediction generation component or the second prediction generation component to determine a second value for the first parameter of the image;

determining, by the one or more computing devices, a first discrepancy between the first value and the second value that exceeds a first discrepancy threshold;

executing, by the one or more computing devices and using the first data as the first input, at least one of the first prediction generation component or the second prediction generation component to determine a third value for a second parameter of the image;

executing, by the one or more computing devices and using the second data as the second input, at least one of the first prediction generation component or the second prediction generation component to determine a fourth value for the second parameter of the image;

determining, by the one or more computing devices, a second discrepancy between the third value and the fourth value is below a second discrepancy threshold; and transmitting, by the one or more computing devices to a computing device for presentation on an interface and based at least in part on determining the first discrepancy and the second discrepancy, an indication of the first discrepancy by excluding the second discrepancy from the indication based at least in part on determining that the second discrepancy is below the second discrepancy threshold.

5. The method of claim 4, wherein the first data comprises an image of a portion of a human subject.

6. The method of claim 4, wherein the first value comprises one of a representation of a probability of a medical condition or a representation of a level of risk of the medical condition.

7. The method of claim 4, wherein at least one of the first prediction generation component or the second prediction generation component is one or more of:

a machine-learned image processing model, or a machine-learned text processing model.

8. The method of claim 4, wherein at least one of the first prediction generation component or the second prediction generation component is one or more of:

a machine-learned image processing model, or an image metadata processing component.

9. The method of claim 4, wherein the second data comprises one or more medical codes indicating one or more medical conditions.

10. The method of claim 4, wherein the first parameter comprises a fault in a physical component represented in the image.

11. The method of claim 4, wherein the first parameter comprises one of:

a demographic attribute of a subject of the image; or a position of the subject of the image relative to an imaging system that captured the image.

12. The method of claim 4, wherein the first data comprises data representing one of an X-ray, a magnetic resonance imaging (MRI) image, a computed tomography (CT) scan image, a computed axial tomography (CAT) scan image, an ultrasound image, a histology image, optical coherence tomography (OCT) image, or a fundus image.

13. A system comprising:

one or more processors; and one or more computer-readable media storing computer-executable instructions that, when executed by the one or more processors, cause a discrepancy determination system to perform operations comprising:

receiving first data of a first modality associated with a human subject and second data of a second modality associated with the human subject;

executing, using the first data as first input, at least one of a first prediction generation component or a second prediction generation component to determine a first value for a first parameter associated with the human subject;

executing, using the second data as second input, at least one of the first prediction generation component or the second prediction generation component to determine a second value for the first parameter associated with the human subject;

determining a first difference between the first value and the second value that satisfies a first discrepancy criterion;

executing, using the first data as the first input, at least one of the first prediction generation component or the second prediction generation component to determine a third value for a second parameter associated with the human subject;

executing, using the second data as the second input, at least one of the first prediction generation component or the second prediction generation component to determine a fourth value for the second parameter associated with the human subject;

determining a second difference between the third value and the fourth value does not satisfy a second discrepancy criterion; and transmitting, to a computing device for presentation on an interface and based at least in part on determining that the first difference between the first value and the second value satisfies the discrepancy criterion, an indication of the first difference by excluding the second difference from the indication based at least in part on determining that the second difference between the third value and the fourth value does not satisfy the second discrepancy criterion.

14. The system of claim 13, wherein the first parameter comprises a medical condition represented in an image associated with the human subject.

15. The system of claim 14, wherein:

the first value is a first representation of a first risk of the human subject having the medical condition; and the second value is a second representation of a second risk of the human subject having the medical condition.

16. The system of claim 15, wherein transmitting the indication of the first difference comprises transmitting instructions to present a graphical representation of a risk scale comprising a first indication of the first risk and a second indication of the second risk.

17. The system of claim 13, wherein transmitting the indication of the first difference comprises determining that the first parameter is represented in a parameter relevance filter.

18. The system of claim 13, wherein one of the first data or the second data comprises digital imaging and communications in medicine (DICOM) data associated with an image associated with the human subject.

19. The system of claim 13, wherein the first data comprises data representing one of an X-ray, a magnetic resonance imaging (MRI) image, a computed tomography (CT) scan image, a computed axial tomography (CAT) scan image, an ultrasound image, a histology image, optical coherence tomography (OCT) image, or a fundus image.

20. The system of claim 13, wherein at least one of the first prediction generation component or the second prediction generation component is one or more of:

a machine-learned image processing model, or a machine-learned text processing model.

\*　\*　\*　\*　\*